US012318063B2

(12) United States Patent
Nishimura

(10) Patent No.: US 12,318,063 B2
(45) Date of Patent: Jun. 3, 2025

(54) ENDOSCOPE CONTROL APPARATUS, ENDOSCOPE CONTROL METHOD, AND STORAGE MEDIUM STORING A PROGRAM

(71) Applicant: OLYMPUS CORPORATION, Tokyo (JP)

(72) Inventor: Hirokazu Nishimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 634 days.

(21) Appl. No.: 17/690,462

(22) Filed: Mar. 9, 2022

(65) Prior Publication Data

US 2022/0192466 A1 Jun. 23, 2022

Related U.S. Application Data

(63) Continuation of application No. PCT/JP2020/033888, filed on Sep. 8, 2020.

(30) Foreign Application Priority Data

Sep. 10, 2019 (WO) .................. PCT/JP2019/035561

(51) Int. Cl.
*A61B 1/00* (2006.01)
*A61B 1/005* (2006.01)
(Continued)

(52) U.S. Cl.
CPC .... *A61B 1/00006* (2013.01); *A61B 1/000096* (2022.02); *A61B 1/0002* (2013.01);
(Continued)

(58) Field of Classification Search
CPC .......... A61B 1/00006; A61B 1/000096; A61B 1/0002; A61B 1/0051; A61B 1/015; A61B 1/045; A61B 1/31; G16H 30/40
See application file for complete search history.

(56) References Cited

U.S. PATENT DOCUMENTS 8,147,402 B2 * 4/2012 Tanaka ................... A61B 5/065
600/117
10,614,597 B2 * 4/2020 Hoelzer ................ G06T 11/006
(Continued)

FOREIGN PATENT DOCUMENTS

JP  H03-165732 A  7/1991
JP  3645223 B2  5/2005
(Continued)

OTHER PUBLICATIONS

International Preliminary Report on Patentability dated Mar. 15, 2022 received in PCT/JP2020/033888.
(Continued)

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

An image acquisition unit acquires an endoscopic image imaged by an endoscope inserted inside a subject. An operation detail determination unit determines one or more operation details from among a predetermined plural number of operation details based on the endoscopic image acquired in the image acquisition unit. An operation control unit controls a movement of the endoscope based on the determined operation details. An operation detail determination unit determines one or more operation details by inputting input data acquired from the endoscopic image acquired in the image acquisition unit to one or more into operation selection models generated by machine learning using, as training data, an image for learning, which is an endoscopic image imaged in the past, and a label indicating an operation detail for an endoscope that has imaged the image for learning.

3 Claims, 16 Drawing Sheets

(51) Int. Cl.
*A61B 1/015* (2006.01)
*A61B 1/045* (2006.01)
*G16H 30/40* (2018.01)
*A61B 1/31* (2006.01)

(52) U.S. Cl.
CPC ............ *A61B 1/0051* (2013.01); *A61B 1/015* (2013.01); *A61B 1/045* (2013.01); *G16H 30/40* (2018.01); *A61B 1/31* (2013.01)

(56) References Cited

U.S. PATENT DOCUMENTS

| | | | | |
|---|---|---|---|---|
| 10,646,288 | B2 * | 5/2020 | Yeung | A61B 5/065 |
| 11,182,878 | B2 * | 11/2021 | Zhang | G01R 33/561 |
| 11,348,243 | B2 * | 5/2022 | Li | G06T 7/0014 |
| 11,532,147 | B2 * | 12/2022 | Barkan | G06N 3/08 |
| 11,910,998 | B2 * | 2/2024 | Ubbesen | A61B 1/00045 |
| 2009/0041320 | A1 * | 2/2009 | Tanaka | G06V 10/52 |
| | | | | 382/128 |
| 2015/0272423 | A1 * | 10/2015 | Ito | A61B 1/00055 |
| | | | | 600/476 |
| 2017/0071504 | A1 * | 3/2017 | Wang | A61B 1/0005 |
| 2017/0337682 | A1 * | 11/2017 | Liao | G06T 7/0012 |
| 2018/0144214 | A1 * | 5/2018 | Hsieh | G06T 7/0002 |
| 2018/0296281 | A1 * | 10/2018 | Yeung | A61B 34/32 |

FOREIGN PATENT DOCUMENTS

| | | |
|---|---|---|
| JP | 2007-090098 A | 4/2007 |
| WO | 2011/040111 A1 | 4/2011 |
| WO | 2018/235185 A1 | 12/2018 |
| WO | 2019/130390 A1 | 7/2019 |
| WO | 2019/155617 A1 | 8/2019 |

OTHER PUBLICATIONS

International Search Report dated Oct. 20, 2020 received in PCT/JP2020/033888.
Japanese Office Action dated Nov. 29, 2022 received in 2021-545540.

* cited by examiner

ANGLE OPERATION UPS LABEL

ANGLE OPERATION RIS LABEL

ANGLE OPERATION DOS LABEL

ANGLE OPERATION LES LABEL

ANGLE OPERATION URS LABEL

ANGLE OPERATION DRS LABEL

ANGLE OPERATION DLS LABEL

ANGLE OPERATION ULS LABEL

ANGLE OPERATION PSS LABEL

PULL OPERATION PLS LABEL

SEARCH OPERATION SES LABEL

PUSH OPERATION PSS_AL LABEL

PUSH OPERATION PSS_AS LABEL

PUSH OPERATION PSS_SH LABEL

PUSH OPERATION PSS_SL LABEL

PUSH OPERATION PSS_TS LABEL

PUSH OPERATION PSS_TL LABEL

ENDOSCOPE CONTROL APPARATUS, ENDOSCOPE CONTROL METHOD, AND STORAGE MEDIUM STORING A PROGRAM

CROSS-REFERENCE TO RELATED APPLICATIONS

This application is a by-pass continuation application of International Application No. PCT/JP2020/033888, filed on Sep. 8, 2020, and claims priority to International Application No. PCT/JP2019/035561, filed on Sep. 10, 2019, the entire contents of each of which are incorporated herein by reference.

BACKGROUND OF THE DISCLOSURE

1. Field of the Invention

The present disclosure relates to an endoscope control apparatus, an endoscope control method, and a storage medium storing a program.

2. Description of the Related Art

In endoscopic observation, a flexible elongated insertion portion is inserted deep inside a subject. In recent years, studies have been conducted on technologies to automate operations on an insertion portion. For example, in an electronic endoscope apparatus in which an insertion portion is provided with a bending portion that can be bent upward, downward, leftward, and rightward, Japanese Patent No. 3645223 discloses a technology for controlling the bending angle of the bending portion such that the distal end of the insertion portion faces the center of the lumen being imaged.

Japanese Patent No. 3645223 does not describe controlling the bending angle of a bending portion in consideration of the presence of structures inside the subject such as folds and intestinal walls. Therefore, according to the technology disclosed in Japanese Patent No. 3645223, when a portion of the lumen being imaged is shielded by a fold located in front of the lumen, a problem may occur in which the distal end of the insertion portion of the endoscope moves in the direction of contacting the fold without avoiding the fold. Further, according to the technology disclosed in Japanese Patent No. 3645223, when a portion of the lumen hidden behind the intestinal wall, a problem may occur in which the distal end of the insertion portion of the endoscope moves in the direction of contacting the intestinal wall without going around the side of the intestinal wall. In other words, according to the technology disclosed in Japanese Patent No. 3645223, there is a problem in which the distal end of the insertion portion cannot be operated properly.

SUMMARY

In this background, a purpose of the present disclosure is to provide an endoscope control apparatus, an endoscope control method, and a storage medium storing a program that are capable of properly operating the distal end of an insertion portion.

An endoscope control apparatus according to one embodiment of the present disclosure includes: an image acquisition unit that acquires an endoscopic image imaged by the endoscope inserted inside a subject; an operation detail determination unit that determines one or more operation details from among a predetermined plural number of operation details based on the endoscopic image acquired in the image acquisition unit; a control unit that controls a movement of the endoscope based on the operation detail determined by the operation detail determination unit. The operation detail determination unit determines one or more operation details by inputting input data acquired from the endoscopic image acquired in the image acquisition unit to one or more into operation selection models generated by machine learning using, as training data, an image for learning, which is an endoscopic image imaged in the past, and a label that is assigned to the image for learning and that indicates an operation detail for an endoscope that has imaged the image for learning.

Another embodiment of the present disclosure relates to a method for controlling a movement of an endoscope, including: acquiring an endoscopic image imaged by the endoscope inserted inside a subject; determining one or more operation details for the endoscope by inputting input data acquired from the endoscopic image into one or more operation selection models generated by machine learning using, as training data, an image for learning, which is an endoscopic image imaged in the past, and a label that is assigned to the image for learning and that indicates an operation detail for an endoscope that has imaged the image for learning; and controlling the movement of the endoscope based on the determined operation details.

Optional combinations of the aforementioned constituting elements and implementations of the present disclosure in the form of methods, apparatuses, systems, recording mediums, and computer programs may also be practiced as additional modes of the present disclosure.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION

The disclosure will now be described by reference to the preferred embodiments. This does not intend to limit the scope of the present disclosure, but to exemplify the disclosure.

Figure 1:
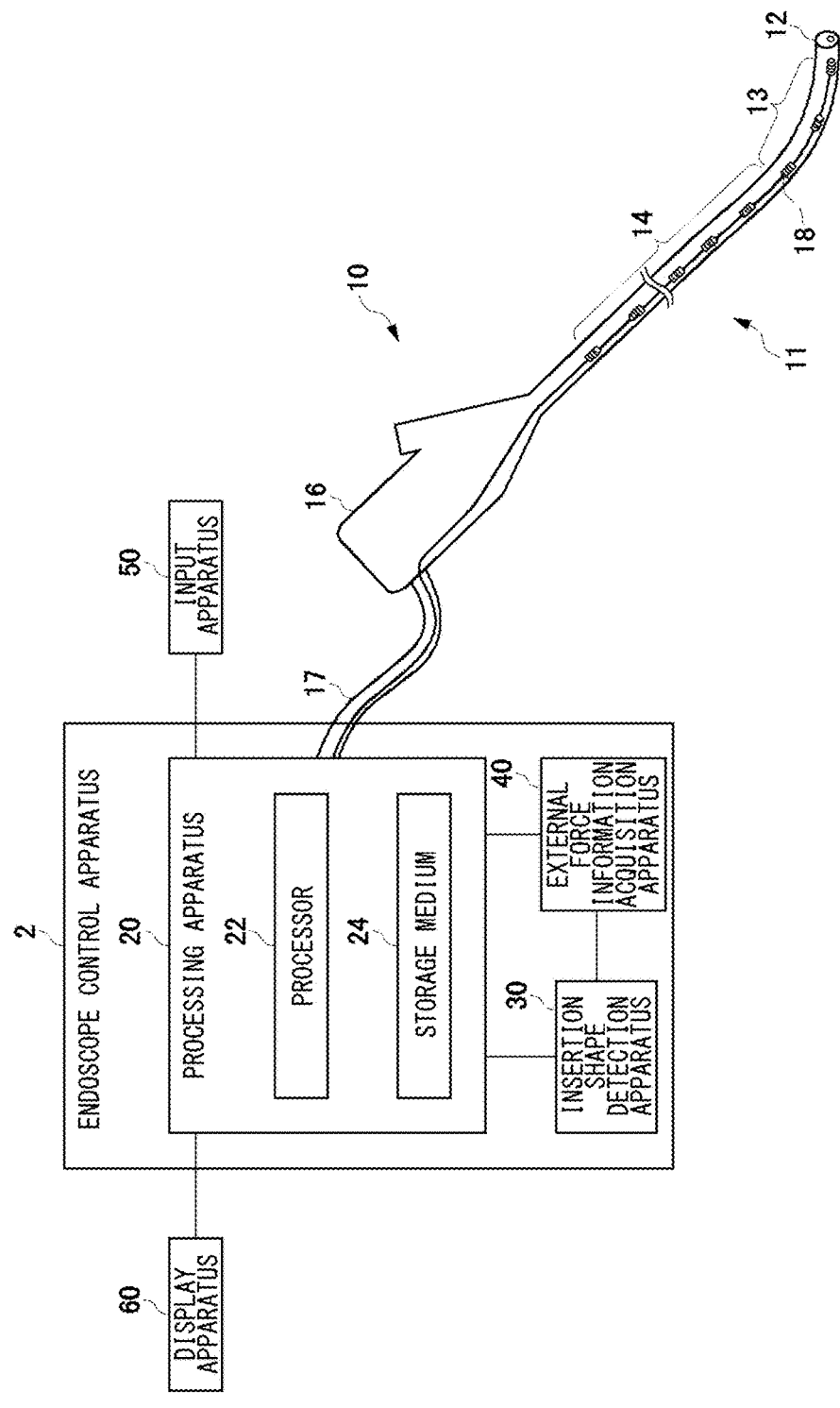
FIG. 1 is a diagram showing the configuration of an endoscope system according to an embodiment.

An embodiment of the present disclosure will be explained in the following with reference to the drawings. FIG. 1 shows the configuration of an endoscope system 1 according to the embodiment. The endoscope system 1 is provided in an endoscopic examination room and includes an endoscope control apparatus 2, an endoscope 10, an input apparatus 50, and a display apparatus 60. The endoscope control apparatus 2 has a processing apparatus 20, an insertion shape detection apparatus 30, and an external force information acquisition apparatus 40 and has a function of automatically operating the movement of the endoscope 10 inserted into the body of the subject. The automatic movement of the endoscope 10 is performed by the processing apparatus 20 including one or more processors 22 and a storage medium 24.

The input apparatus 50 is an input interface operated by a user and is formed to output an instruction according to the user's operation to the processing apparatus 20. The input apparatus 50 may include, for example, an operation apparatus such as a mouse, a keyboard, a touch panel, and the like. The display apparatus 60 is a device that displays on a screen an endoscopic image or the like output from the processing apparatus 20 and may be a liquid crystal display or an organic EL display.

The endoscope 10 is provided with an imaging unit that includes a solid-state imaging device (for example, CCD image sensor or CMOS image sensor). The solid-state imaging device converts incident light into an electrical signal and outputs the electrical signal to the processing apparatus 20. The processing apparatus 20 has an image processing unit that performs signal processing such as A/D conversion, noise removal, and the like on an imaging signal photoelectrically converted by the solid-state imaging device, and generates an endoscopic image. The image processing unit may be installed on the endoscope 10 side, and the endoscope 10 may generate the endoscopic image. The processing apparatus 20 displays video imaged by the endoscope 10 on the display apparatus 60 in real time.

The endoscope 10 includes an insertion portion 11 to be inserted into the subject, an operation unit 16 provided on the base end side of the insertion portion 11, and a universal cord 17 extending from the operation unit 16. The endoscope 10 is detachably connected to the processing apparatus 20 by a scope connector (not shown) provided at an end of the universal cord 17.

The insertion portion 11 having an elongated shape has a rigid distal end 12, a bending portion 13 formed to be freely bendable, and a long flexible tube 14 having flexibility, in order from the distal end side to the base end side. Inside the distal end 12, the bending portion 13, and the flexible tube 14, there are a plurality of source coils 18, which generate a magnetic field according to a coil drive signal supplied from the processing apparatus 20, are arranged at predetermined intervals along the longitudinal direction of the insertion portion 11.

In the endoscope system 1 according to the embodiment, the processing apparatus 20 automatically operates the endoscope 10 so as to control the movement of the endoscope 10 inside the subject. Alternatively, it is also possible for the user to hold the operation unit 16 and manually operate the endoscope 10.

The basic operations on the endoscope 10 include the following:

"Push operation" for moving the insertion portion 11 forward

"Pull operation" for moving the insertion portion 11 backward

"Angle operation" for bending the bending portion 13

"Twist operation" for rotating the insertion portion 11 around the insertion axis "Air feeding operation" for insufflating air or gas in a forward direction of the distal end 12

"Water feeding operation" for infusing water in a forward direction of the distal end 12

"Suction operation" for suctioning objects such as tissue fragments that are present near the distal end 12

"Search operation" for searching a lumen by bending the bending portion 13 in multiple directions so as to point the distal end 12 in multiple directions When a user such as a physician (or a doctor, or a colonoscopist) operates the release switch of the endoscope 10 while the endoscope 10 is being inserted into the subject, the processing apparatus 20 captures an endoscopic image at the time when the release switch is operated and transmits the endoscopic image to an image server (not shown) for recording. The release switch may be provided on the input apparatus 50. A light guide (not shown) for transmitting illumination light supplied from the processing apparatus 20 so as to illuminate the inside of the subject is provided inside the endoscope 10. The distal end 12 is provided with an illumination window for emitting the illumination light transmitted by the light guide to the subject and an imaging unit for imaging the subject at a predetermined cycle and outputting an imaging signal.

The operation unit 16 is provided with an operation member for the user to operate the endoscope 10. The operation unit 16 includes an angle knob for bending the bending portion 13 in at least four directions: upward; downward; leftward; and rightward that intersect with the longitudinal axis of the insertion portion 11. The operation unit 16 may include one or more release switches for the user to input an instruction for imaging.

The processing apparatus 20 is detachably connected to each structure of an insertion shape detection apparatus 30, an external force information acquisition apparatus 40, an input apparatus 50, and a display apparatus 60. The processing apparatus 20 receives an instruction input by the user through the input apparatus 50 and performs a process that corresponds to the instruction. The processing apparatus 20 acquires an imaging signal periodically output from the endoscope 10 and displays an endoscopic image on the display apparatus 60.

In the embodiment, the processing apparatus 20 has a function of generating and outputting a control signal for controlling the movement of the endoscope 10. More specifically, the processing apparatus 20 is formed so as to automatically operate the movement of the endoscope 10 based on an endoscopic image generated based on an imaging signal output from the endoscope 10.

The insertion shape detection apparatus 30 has a function of detecting a magnetic field generated by each of the plurality of source coils 18 provided in the insertion portion 11 and acquiring the position of each of the plurality of source coils 18 based on the intensity of the detected magnetic field. The insertion shape detection apparatus 30 generates insertion shape information indicating the acquired positions of the plurality of source coils 18 and outputs the insertion shape information to the processing apparatus 20 and the external force information acquisition apparatus 40.

The external force information acquisition apparatus 40 stores data on the curvature (or radius of curvature) and bending angle of a predetermined plurality of positions of the insertion portion 11 in a state where no external force is applied and data on the curvature (or radius of curvature) and bending angle of the predetermined plurality of positions of the insertion portion 11 obtained in a state where a predetermined external force is applied to an arbitrary position of the insertion portion 11 from any conceivable direction. The external force information acquisition apparatus 40 identifies the positions of the plurality of source coils 18 provided in the insertion portion 11 based on the insertion shape information output from the insertion shape detection apparatus 30 and acquires the curvature (or radius of curvature) and the bending angle at each position of the plurality of source coils 18. The external force information acquisition apparatus 40 may acquire external force information indicating the magnitude and direction of the external force at each position of the plurality of source coils 18 from the acquired curvature (or radius of curvature) and bending angle and from various data stored in advance. The external force information acquisition apparatus 40 outputs the acquired external force information to the processing apparatus 20.

In the embodiment, the method disclosed in Japanese Patent No. 5851204 or the method disclosed in Japanese Patent No. 5897092 may be used as the method for the external force information acquisition apparatus 40 to calculate external force at each position of the plurality of source coils 18 provided in the insertion portion 11. Further, electronic components such as a strain sensor, a pressure sensor, an acceleration sensor, a gyroscope sensor, and a wireless element may be installed in the insertion portion 11, and the external force information acquisition apparatus 40 may be formed to calculate the external force at each position of the plurality of source coils 18 based on signals output from the electronic components.

The processing apparatus 20 according to the embodiment performs control of automatically operating the movement of the insertion portion 11 of the endoscope 10. In the following, before explaining the automatic operation control technology according to the embodiment, a comparative technology for the comparison with the control technology according to the embodiment will be explained.

<Explanation of Comparative Technology>

First, manual operation of an endoscope by a physician will be discussed. The physician operates the endoscope based on various decisions when advancing the distal end of the endoscope toward the lumen. More specifically, looking at an endoscopic image, the physician instantly decides to, for example, avoid an obstacle that exists in front of the lumen, avoid contact of the distal end of the endoscope with the mucosal surface, not place a load on the intestinal tract, and decide on the current path in anticipation of the path ahead and operates the endoscope.

Figure 2A:
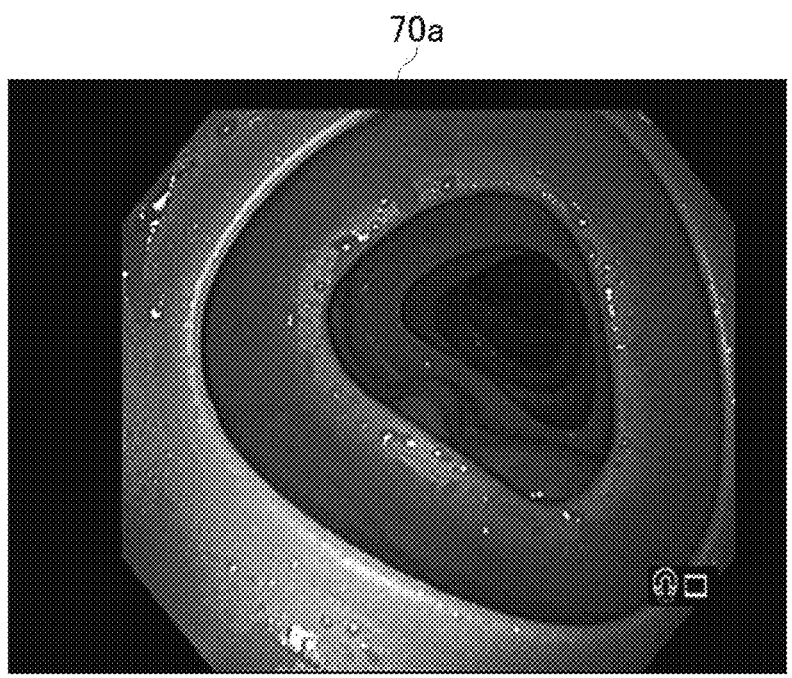
FIGS. 2A and 2B are diagrams showing examples of endoscopic images.

FIG. 2A shows an example of an endoscopic image. An endoscopic image 70a is an image of an anatomic colon model formed of rubber (rubber intestine) imaged by an endoscope. Upon confirming that the lumen is in the center of the image while looking at the endoscopic image 70a, the physician decides that the distal end of the endoscope may be advanced and moves the distal end of the endoscope forward.

Figure 2B:
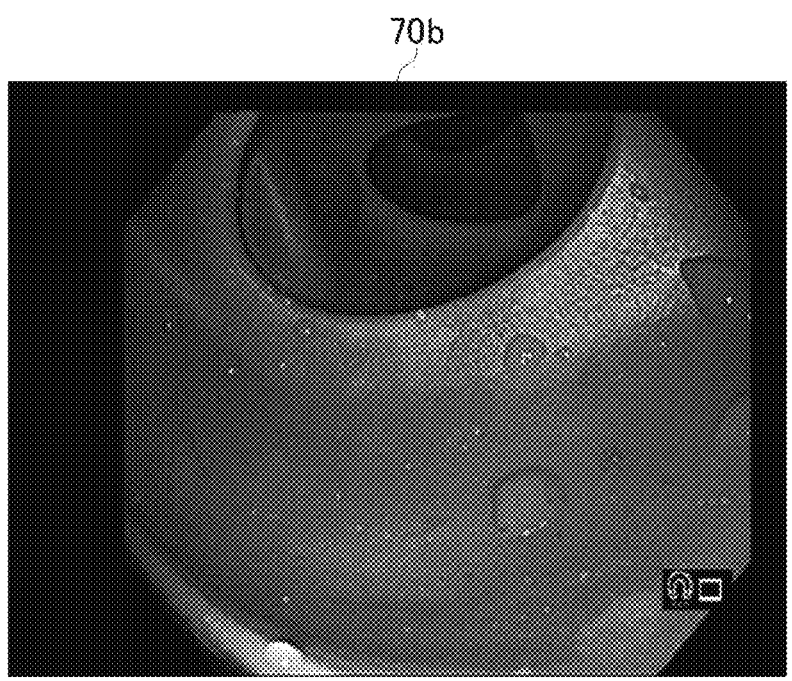

FIG. 2B shows another example of an endoscopic image. An endoscopic image 70b is also an image obtained by imaging a rubber intestine. Upon confirming that the lumen is in the upper part of the image while looking at the endoscopic image 70b, the physician decides that the distal end of the endoscope will come into contact with a fold in front of the distal end of the endoscope if the distal end is moved forward in this state. Thus, the physician operates the angle knob to bend the bending portion 13 upward such that the lumen is imaged in the center of the image. When the lumen is imaged in the center of the image, since the state is the same as the state in the endoscopic image 70a shown in FIG. 2A, the physician decides that the distal end of the endoscope may be advanced and moves the distal end of the endoscope forward.

The above decisions and operations can be easily performed only by a physician, and a complicated procedure is required to realize the determinations and operations by an apparatus. An automatic operation method for realizing manual operation equivalent to that by a physician will be explained as a comparative technology for comparison with the embodiment in the following. The comparative technology is implemented by the following steps.

(S1) Acquire a target endoscopic image.

(S2) Perform region division based on color tone, edge, shape information, and other feature amounts contained in the endoscopic image.

(S3) Classify each divided region into a variety of structures such as a lumen, a fold, mucosa, and a residue.

(S4) Identify a scene included in the endoscopic image based on the classification results in S3.

This scene is a predefined scene, for example, the lumen is included in a front part, the lumen is included in an upper part, the lumen is included in a lower part, there is an obstacle in front of the lumen, the lumen is not imaged, and so on.

(S5) Assign an operation detail to each scene in advance and determine the operation detail based on the scene classified in S4.

As an example, the procedure for processing the endoscopic image 70a shown in FIG. 2A in the comparative technology will be explained. In the comparative technology, after the endoscopic image 70a is acquired (S1), a region division process is performed (S2) and a luminal region, a contour line of a fold, a mucosal surface region, etc., are identified in the endoscopic image 70a (S3). Then, in the comparative technology, the position and shape of the lumen, the absence of obstacles in front of the lumen, etc., are recognized in the image, and the endoscopic image 70a is identified to include a scene of "the lumen is included in a front part" (S4). In the comparative technology, the defined scene and the operation detail of the endoscope are associated with each other in advance, and the scene of "the lumen is included in a front part" is associated with the "push operation" on the endoscope. Therefore, according to the comparative technology, by performing image analysis of the endoscopic image 70a, the "push operation" on the endoscope is determined as the operation to be performed next (S5).

In the case of processing the endoscopic image 70b shown in FIG. 2B, in the comparative technology, after the endoscopic image 70b is acquired (S1), a region division process is performed (S2) and a luminal region, a contour line of a fold, a mucosal surface region, etc., are identified in the endoscopic image 70b (S3). In the comparative technology, the position and shape of the lumen, the absence of obstacles in front of the lumen, etc., are recognized in the image, and the endoscopic image 70b is identified to include a scene of "the lumen is included in an upper part" (S4). The scene of "the lumen is included in an upper part" is associated with "upward angle operation" on the endoscope. Therefore, according to the comparative technology, by performing image analysis of the endoscopic image 70b, the "upward angle operation" on the endoscope is determined as the operation to be performed next (S5).

As described above, the endoscopic images 70a and 70b shown in FIGS. 2A and 2B are processed in a relatively easy manner by the comparative technology. The processing of another endoscopic image by the comparative technology will be explained in the following.

Figure 3A:
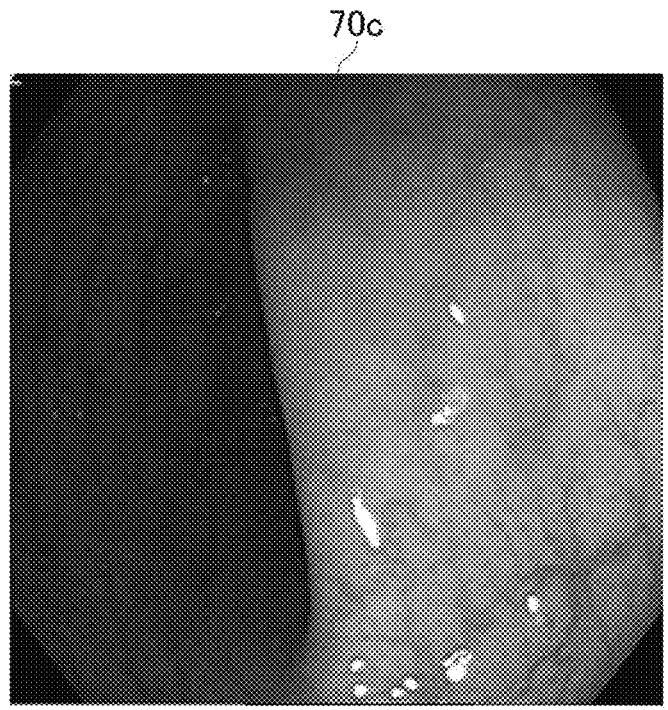
FIGS. 3A and 3B are diagrams showing examples of endoscopic images.

FIG. 3A shows another example of an endoscopic image. An endoscopic image 70c is an image of a bend of the subject's colon. Although the lumen is not clearly imaged in the endoscopic image 70c, a physician can find a path that allows the distal end of the endoscope to move around from the left side and enter the lumen of the bend since the right side of the endoscopic image 70c is bright. Therefore, in a state where the endoscopic image 70c is being displayed, it is necessary to first turn the distal end of the endoscope to the left.

In order to achieve the determination of this operation using the comparative technology, it is necessary to define a scene in which "the left side is dark, the right side is bright, and the lumen is hidden due to bending" and further associate "leftward angle operation" of the endoscope with the scene in advance. By preparing the definition and association in advance, the comparative technology allows "leftward angle operation" to be determined as operation to be performed next based on the endoscopic image 70c in FIG. 3A.

Figure 3B:
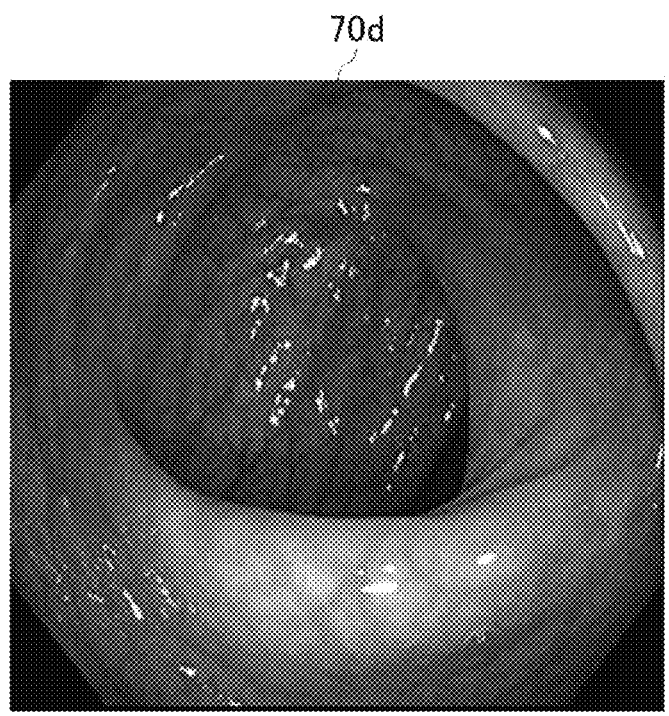

FIG. 3B shows another example of an endoscopic image. The endoscopic image 70d is an image obtained by imaging the lumen of the subject, and the lumen is imaged at a position slightly lower right of the center. However, when an angle operation in the lower right direction is performed on the endoscope, the distal end of the endoscope may come into contact with the mucosal surface of a fold that exists in the lower right side of the image. In this case, a physician can avoid contact between the distal end of the endoscope and the mucosal surface of the fold by first performing an angle operation in the upper left direction, then advancing the endoscope, and then further performing an angle operation in the lower right direction on the endoscope. Therefore, in a state where the endoscopic image 70d is being displayed, it is necessary to first perform the operation of pointing the distal end of the endoscope in the upper left direction.

In order to achieve the determination of this operation using the comparative technology, it is necessary to define a scene in which "lumen is in a lower right position and the distal end of the endoscope located close to the mucosal surface of the fold" and further associate "angle operation in the upper left direction" of the endoscope with the scene in advance. By preparing these definition and association in advance, the comparative technology allows "angle operation in the upper left direction" to be determined as operation to be performed next based on the endoscopic image 70d in FIG. 3B.

As described above, in the comparative technology, it is not easy to define an appropriate scene according to the situation in advance, especially in the scene identification process in S4, and an algorithm including that for a scene recognition method is very complicated and highly difficult to implement. Actually, it is also a very difficult task to associate an operation detail with each defined scene.

Based on the above premise, the automatic operation control technology for the endoscope 10 in the embodiment will be explained. According to the control technology in the embodiment, the scene identification process in S4 in the comparative technology is unnecessary, and the task of associating a scene to an operation detail is also unnecessary. Thus, the control technology has the advantage of omitting the construction of a complicated and highly difficult algorithm.

Figure 4:
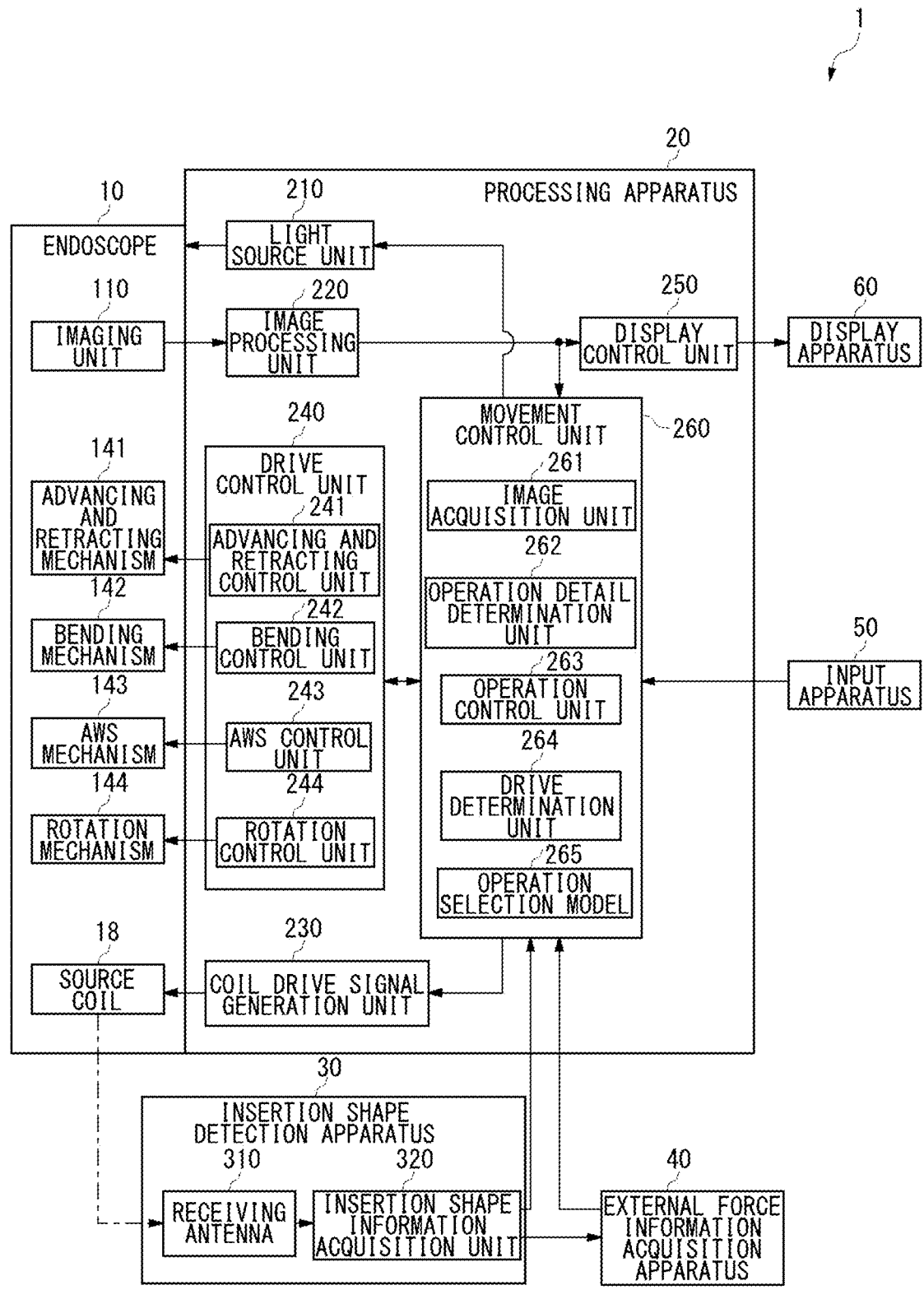
FIG. 4 is a functional block diagram of the endoscope system according to the embodiment.

FIG. 4 is a functional block diagram for explaining the configuration of the endoscope system 1 according to the embodiment. The endoscope system 1 includes an endoscope 10, a processing apparatus 20, an insertion shape detection apparatus 30, an external force information acquisition apparatus 40, an input apparatus 50, and a display apparatus 60.

The configuration shown in FIG. 4 is implemented by hardware such as one or more processors 22, memory, auxiliary storage, or other LSIs and by software such as a program or the like loaded into the memory. The figure depicts functional blocks implemented by the cooperation of hardware and software. Thus, a person skilled in the art should appreciate that there are many ways of accomplishing these functional blocks in various forms in accordance with the components of hardware only, software only, or the combination of both. For example, a program for executing at least some of the functions of the processing apparatus 20 is stored in a storage medium 24, and a processor 22 may load the program from the storage medium 24 into the memory to realize each function of the processing apparatus 20.

The insertion shape detection apparatus 30 includes a receiving antenna 310 and an insertion shape information acquisition unit 320. The receiving antenna 310 is formed having a plurality of coils that detect a magnetic field generated by each of the plurality of source coils 18 in a three-dimensional manner. Upon detecting the magnetic field generated by each of the plurality of source coils 18, the receiving antenna 310 outputs a magnetic field detection signal corresponding to the intensity of the detected magnetic field to the insertion shape information acquisition unit 320.

The insertion shape information acquisition unit 320 acquires the position of each of the plurality of source coils 18 based on a magnetic field detection signal output from the receiving antenna 310. The insertion shape information acquisition unit 320 generates insertion shape information indicating the position of each of the plurality of source coils 18 and outputs the insertion shape information to a movement control unit 260 and the external force information acquisition apparatus 40.

More specifically, as the respective positions of the plurality of source coils 18, the insertion shape information acquisition unit 320 acquires a plurality of three-dimensional coordinate values in a virtual spatial coordinate system with the origin or reference point at a predetermined position (such as the anus) of the subject. The insertion shape information acquisition unit 320 generates insertion shape information including the three-dimensional coordinate values of the plurality of source coils 18 and outputs the insertion shape information to the movement control unit 260 and the external force information acquisition apparatus 40.

The external force information acquisition apparatus 40 acquires the curvature (or radius of curvature) and the bending angle at each position of the plurality of source coils 18 based on the insertion shape information output from the insertion shape detection apparatus 30. The external force information acquisition apparatus 40 may acquire external force information indicating the magnitude and direction of the external force at each position of the plurality of source coils 18 from the acquired curvature (or radius of curvature) and bending angle and from various data stored in advance.

The external force information acquisition apparatus 40 outputs the acquired external force information to the movement control unit 260.

The endoscope 10 includes a source coil 18, an imaging unit 110, an advancing and retracting mechanism 141, a bending mechanism 142, an AWS mechanism 143, and a rotation mechanism 144. The advancing and retracting mechanism 141, the bending mechanism 142, the AWS mechanism 143, and the rotation mechanism 144 form a movement mechanism in the endoscope 10.

The imaging unit 110 has an observation window through which return light from the subject illuminated by illumination light enters and a solid-state imaging device (e.g., a CCD image sensor or a CMOS image sensor) that images the return light and outputs an imaging signal.

The advancing and retracting mechanism 141 has a mechanism for realizing the movement of advancing and retracting the insertion portion 11. For example, the advancing and retracting mechanism 141 may be formed having a pair of rollers respectively arranged at opposite positions across the insertion portion 11 and a motor for rotating the pair of rollers. The advancing and retracting mechanism 141 drives the motor in response to an advancing and retracting control signal output from the processing apparatus 20 so as to rotate the pair of rollers, thereby selectively executing either one of the movement of advancing the insertion portion 11 and the movement of retracting the insertion portion 11.

The bending mechanism 142 has a mechanism for realizing the movement of bending the bending portion 13. For example, the bending mechanism 142 may be formed having a plurality of bending pieces provided in the bending portion 13, a plurality of wires connected to the plurality of bending pieces, and a motor for pulling the plurality of wires. The bending mechanism 142 drives the motor in response to a bending control signal output from the processing apparatus 20 so as to change the amount of pulling of the plurality of wires, thereby allowing for the bending of the bending portion 13 in any of at least four directions: upward; downward; leftward; and rightward that intersect with the longitudinal axis of the insertion portion 11. The bending portion 13 according to the embodiment may have a structure that bends in any of eight directions that intersect with the longitudinal axis of the insertion portion 11.

An air feeding, water feeding, and suction (AWS) mechanism 143 has a mechanism for realizing air feeding, water feeding, and suction movements. For example, the AWS mechanism 143 may be formed having two pipelines, an air and water feeding pipeline and a suction pipeline provided inside the insertion portion 11, the operation unit 16, and the universal cord 17 and a solenoid valve that performs a movement of opening one of the two pipelines while closing the other.

When activating the solenoid valve to open the air and water feeding pipeline in response to an AWS control signal output from the processing apparatus 20, the AWS mechanism 143 causes fluid including at least one of water and air supplied from the processing apparatus 20 to circulate into the air and water feeding pipeline and then discharge the fluid from an outlet port formed in the distal end 12. Further, when activating the solenoid valve to open the suction pipeline in response to the AWS control signal output from the processing apparatus 20, the AWS mechanism 143 applies a suction force generated by the processing apparatus 20 to the suction pipeline and suctions an object that exists near a suction port formed at the distal end 12 by the suction force.

The rotation mechanism 144 has a mechanism for realizing a movement of rotating the insertion portion 11 using the insertion axis of the insertion portion 11 as the rotation axis. For example, the rotation mechanism 144 may be formed having a support member that rotatably supports the insertion portion 11 on the base end side of the flexible tube 14 and a motor for rotating the support member. The rotation mechanism 144 rotates the insertion portion 11 around the insertion axis by driving the motor in response to a rotation control signal output from the processing apparatus 20 so as to rotate the support member. In the embodiment, the insertion axis of the insertion portion 11 may be the central axis in the longitudinal direction of the insertion portion 11.

The processing apparatus 20 includes a light source unit 210, an image processing unit 220, a coil drive signal generation unit 230, a drive control unit 240, a display control unit 250, and a movement control unit 260.

The light source unit 210 generates illumination light for illuminating the inside of the subject and supplies the illumination light to the endoscope 10. The light source unit 210 may have one or more LEDs or one or more lamps as a light source. The light source unit 210 may change the amount of the illumination light in response to a movement control signal supplied from the movement control unit 260.

The image processing unit 220 has a signal processing circuit, performs a predetermined process on an imaging signal output from the endoscope 10 so as to generate an endoscopic image, and outputs the generated endoscopic image to the display control unit 250 and the movement control unit 260.

The coil drive signal generation unit 230 generates a coil drive signal for driving the source coil 18. The coil drive signal generation unit 230 has a drive circuit, generates a coil drive signal in response to a movement control signal supplied from the movement control unit 260, and supplies the coil drive signal to the source coil 18.

The drive control unit 240 generates a control signal corresponding to a basic operation on the endoscope 10 based on a movement control signal supplied from the movement control unit 260 and drives the movement mechanism in the endoscope 10. More specifically, the drive control unit 240 controls at least one of the following operations: an advancing and retracting movement by the advancing and retracting mechanism 141, a bending movement by the bending mechanism 142, and an AWS movement by the AWS mechanism 143, and a rotation movement by the rotation mechanism 144. The drive control unit 240 includes an advancing and retracting control unit 241, a bending control unit 242, an AWS control unit 243, and a rotation control unit 244.

The advancing and retracting control unit 241 generates and outputs an advancing and retracting control signal for controlling the movement of the advancing and retracting mechanism 141 based on the movement control signal supplied from the movement control unit 260. More specifically, the advancing and retracting control unit 241 generates and outputs an advancing and retracting control signal for controlling the rotation of a motor provided in the advancing and retracting mechanism 141 based on the movement control signal supplied from the movement control unit 260.

The bending control unit 242 generates and outputs a bending control signal for controlling the movement of the bending mechanism 142 based on the movement control signal supplied from the movement control unit 260. More specifically, the bending control unit 242 generates and outputs a bending control signal for controlling the rotation of a motor provided in the bending mechanism 142 based on the movement control signal supplied from the movement control unit 260.

By controlling a pump, etc., not shown in the figure based on the movement control signal supplied from the movement control unit 260, the AWS control unit 243 selectively executes either one of a movement for supplying fluid including at least one of water and air to the endoscope 10 and a movement for generating suction force for suctioning an object existing near the suction port of the distal end 12.

The AWS control unit 243 is formed to generate and output an AWS control signal for controlling the movement of the AWS mechanism 143. More specifically, the AWS control unit 243 generates and outputs an AWS control signal for controlling the movement status of the solenoid valve provided in the AWS mechanism 143 based on the movement control signal supplied from the movement control unit 260.

The rotation control unit 244 generates and outputs a rotation control signal for controlling the movement of the rotation mechanism 144 based on the movement control signal supplied from the movement control unit 260. More specifically, the rotation control unit 244 generates and outputs a rotation control signal for controlling the rotation of a motor provided in the rotation mechanism 144 based on the movement control signal supplied from the movement control unit 260.

The display control unit 250 generates a display image including an endoscopic image output from the image processing unit 220 and displays the generated display image on the display apparatus 60.

The movement control unit 260 has a function of generating a movement control signal for making the endoscope 10 perform a movement in accordance with an instruction, etc., from the operation unit 16 and the input apparatus 50 and outputting the movement control signal to the drive control unit 240. Further, when an automatic insertion mode of the endoscope 10 is set to ON, the movement control unit 260 has a function of automatically controlling the movement of the endoscope 10 based on the endoscopic image generated by the image processing unit 220. The movement control unit 260 includes an image acquisition unit 261, an operation detail determination unit 262, an operation control unit 263, a drive determination unit 264, and an operation selection model 265.

The image acquisition unit 261 acquires an endoscopic image imaged by the endoscope 10 that is being inserted inside the subject from the image processing unit 220. The imaging unit 110 of the endoscope 10 supplies an imaging signal at a predetermined cycle (e.g. 30 frames/second) to the image processing unit 220. The image processing unit 220 generates an endoscopic image from the imaging signal and supplies the endoscopic image to the image acquisition unit 261. Therefore, the image acquisition unit 261 acquires an endoscopic image at a predetermined cycle.

The operation detail determination unit 262 has a function of determining one or more operation details from among a predetermined plural number of operation details based on the endoscopic image acquired in the image acquisition unit 261. In other words, the operation detail determination unit 262 determines the operation detail to be performed next from among a plurality of endoscopic operation options based on the endoscopic image that has imaged the inside of the subject. The predetermined plural number of operation details may be formed by at least one kind of the basic operations described above: the push operation, the pull operation, the angle operation, the twist operation, the air feeding operation, the water feeding operation, and the suction operation.

In the embodiment, at each time when the image acquisition unit 261 acquires an endoscopic image, the operation detail determination unit 262 may determine the operation detail of the endoscope 10, and the operation control unit 263 may generate a movement control signal according to the determined operation detail and supplies the movement control signal to the drive control unit 240.

As another timing example, the drive control unit 240 may drive the movement mechanism of the endoscope 10 based on the movement control signal from the operation control unit 263, and when the driving is completed, the operation detail determination unit 262 may determine the operation detail for the endoscope 10 using the endoscopic image acquired by the image acquisition unit 261, and the operation control unit 263 may generate a movement control signal.

For example, when the drive control unit 240 is driving and controlling the movement mechanism of the endoscope 10, the drive determination unit 264 determines that the drive control unit 240 is driving and controlling the movement mechanism. Upon the ending of the drive control by the drive control unit 240, the drive determination unit 264 determines that the drive control has ended. At this time, the drive determination unit 264 notifies the operation detail determination unit 262 that a new operation detail should be determined, and the operation detail determination unit 262 determines the operation detail of the endoscope 10 using the newly acquired endoscopic image. In this way, the operation detail determination unit 262 may determine the operation detail of the endoscope 10 based on the endoscopic image acquired by the image acquisition unit 261 after or immediately before the completion of driving the movement mechanism.

By inputting input data acquired from the endoscopic image acquired in the image acquisition unit 261 to the operation selection model 265, the operation detail determination unit 262 determines an appropriate operation detail for the endoscope 10 imaging the endoscopic image. The operation selection model 265 is a learned model generated by machine learning using an image for learning, which is an endoscopic image imaged in the past, and a label indicating an operation detail for an endoscope that has imaged the image for learning, as training data.

In the embodiment, the operation selection model 265 is generated through the learning of each coupling coefficient (weight) in a convolutional neutral network (CNN) corresponding to a multilayer neural network including an input layer, one or more convolutional layers, an output layer by a learning method such as deep learning.

First Exemplary Embodiment

In the generation of the operation selection model 265, machine learning using training data that includes images for learning, which is an endoscopic image of the inside of a human intestine or a colon model imaged by an endoscope in the past, and a label indicating which of the five operation details is most suitable for a situation shown by the image for learning.

The five operation details include an angle operation UPS for pointing the distal end 12 upward by bending the bending portion 13, an angle operation DOS for pointing the distal end 12 downward by bending the bending portion 13, an angle operation LES for pointing the distal end 12 leftward by bending the bending portion 13, an angle operation RIS for pointing the distal end 12 rightward by bending the bending portion 13, and an angle maintenance operation AMS for maintaining the direction of the distal end 12 to be the current direction by fixing the bending angle of the bending portion 13.

In all the exemplary embodiments, the up-and-down direction of the distal end 12 is set as a direction orthogonal to the insertion axis of the insertion portion 11 and is also set as a direction corresponding to the vertical direction of the solid-state imaging device provided in the imaging unit 110. Also, in all the exemplary embodiments, the crosswise direction of the distal end 12 is set as a direction orthogonal to the insertion axis of the insertion portion 11 and is also set as a direction corresponding to the horizontal direction of the image sensor provided in the imaging unit 110. Therefore, in the exemplary embodiments, the up-and-down direction of the distal end 12 matches the up-and-down direction of an endoscopic image output from the image processing unit 220, and the crosswise direction of the distal end 12 matches the crosswise direction of an endoscopic image output from the image processing unit 220.

At the time of generating the training data, a knowledgeable person looks at the image for learning, subjectively selects one operation detail that is most likely to be performed in a situation shown in the image for learning from among the five operation details described above, and assigns a label of the selected operation detail to the image for learning. The knowledgeable person may be a physician. For example, when the endoscopic image 70b shown in FIG. 2B is an image for learning, since the lumen exists in the upper part of the image, the knowledgeable person determines that an operation of pointing the distal end of the endoscope upward, that is, the angle operation UPS, should be performed and assigns an angle operation UPS label to the endoscopic image 70b. This label assigning task is performed on a large number of past endoscopic images, thereby generating the training data.

Figure 5:
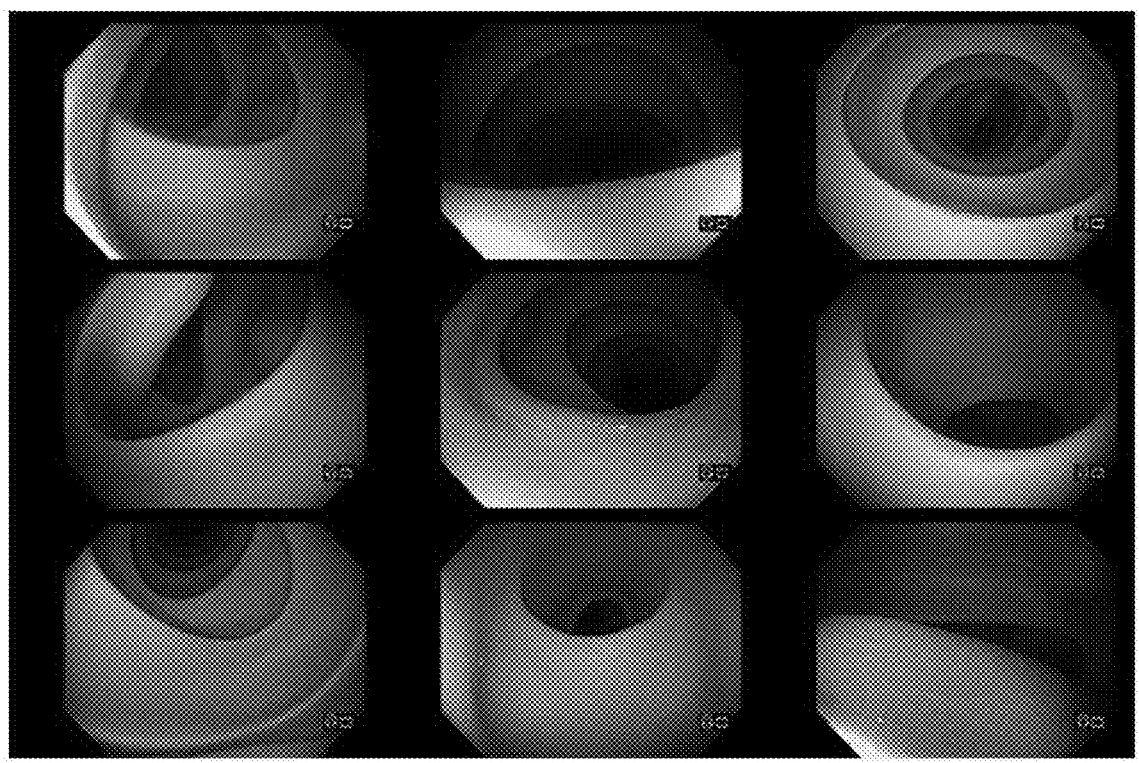
FIG. 5 shows an example of a training data set.

An example of training data including an image for learning and a label is shown below. FIG. 5 shows an example of a training data set. To all images for learning shown in FIG. 5, "angle operation UPS label" indicating an upward angle operation is assigned. The images for learning shown in FIG. 5 are images for which it has been decided that the bending portion 13 should be bent in the upward direction as an endoscope operation to be performed next.

Figure 6:
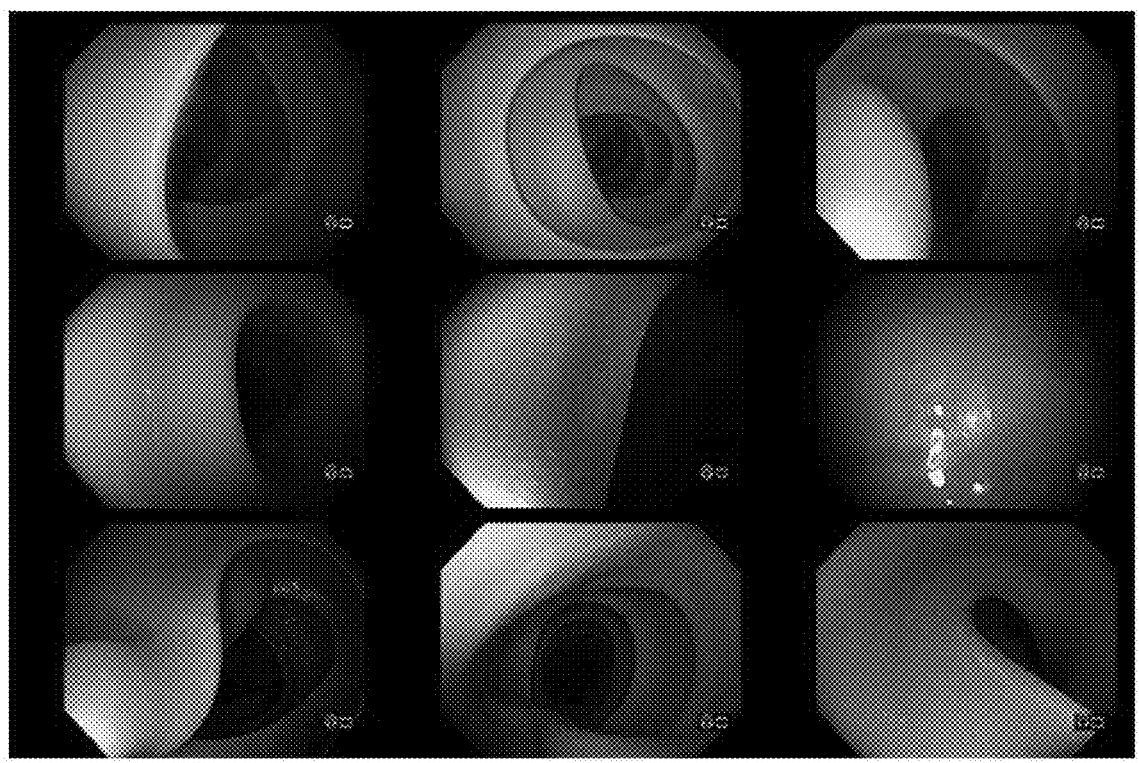
FIG. 6 shows an example of a training data set.

FIG. 6 shows another example of the training data set. To all images for learning shown in FIG. 6, "angle operation RIS label" indicating a rightward angle operation is being assigned. The images for learning shown in FIG. 6 are images for which it has been decided that the bending portion 13 should be bent in the rightward direction as an endoscope operation to be performed next.

Figure 7:
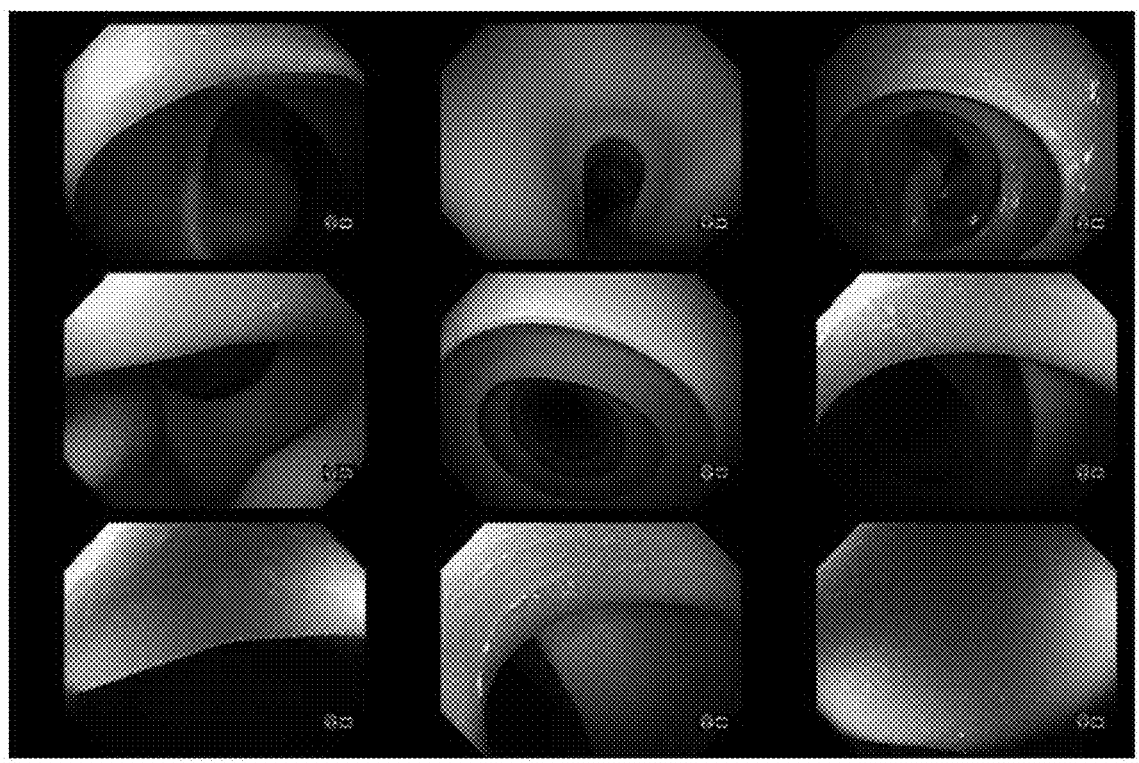
FIG. 7 shows an example of a training data set.

FIG. 7 shows another example of the training data set. To all images for learning shown in FIG. 7, "angle operation DOS label" indicating a downward angle operation is being assigned. The images for learning shown in FIG. 7 are images for which it has been decided that the bending portion 13 should be bent in the downward direction as an endoscope operation to be performed next.

Figure 8:
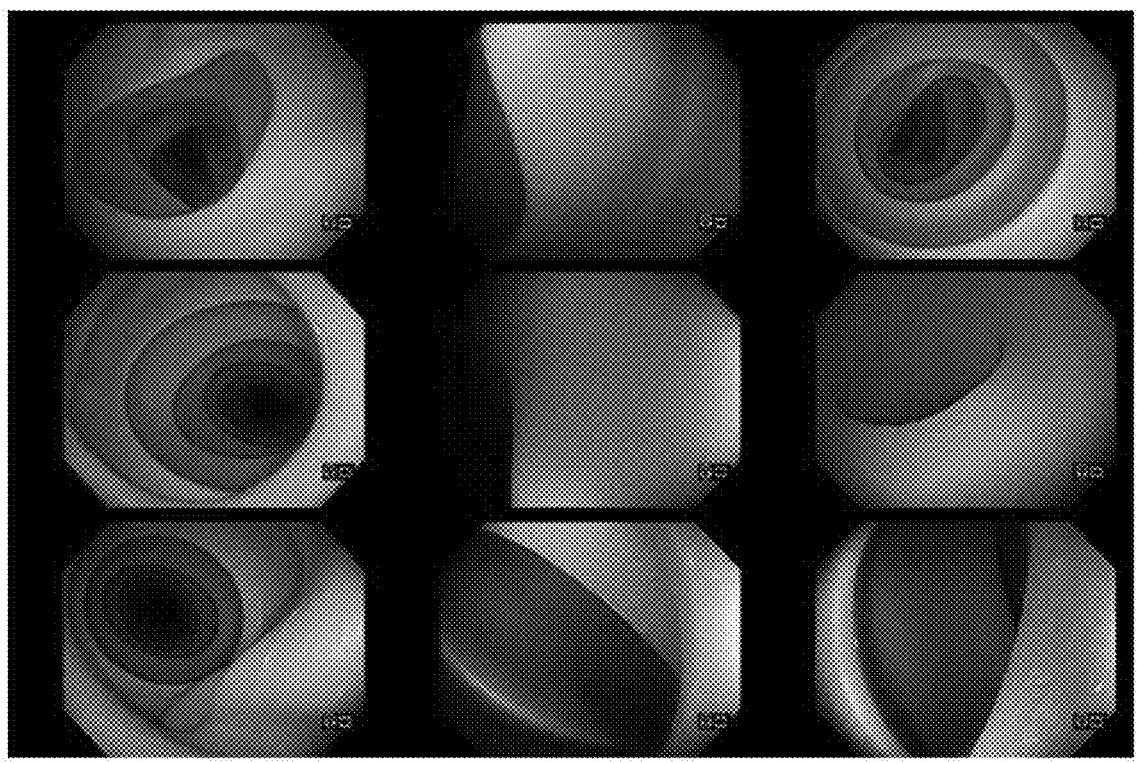
FIG. 8 shows an example of a training data set.

FIG. 8 shows another example of the training data set. To all images for learning shown in FIG. 8, "angle operation LES label" indicating a leftward angle operation is being assigned. The images for learning shown in FIG. 8 are images for which it has been decided that the bending portion 13 should be bent in the leftward direction as an endoscope operation to be performed next.

Illustration is omitted for training data of the angle maintenance operation AMS for maintaining the direction of the distal end 12 to be the current direction by fixing the bending angle of the bending portion 13. However, for example, a label for "angle maintenance operation AMS" may be assigned to an image for learning shown in FIG. 13 later. The operation selection model 265 according to the first exemplary embodiment is generated by machine learning using at least the training data sets shown in FIGS. 5 to 8.

The operation detail determination unit 262 determines one or more operation details by inputting input data acquired from an endoscopic image acquired in the image acquisition unit 261 to one or more into operation selection models 265 generated by machine learning using, as training data, an image for learning and a label indicating an operation detail for an endoscope that has imaged the image for learning. More specifically, the operation detail determination unit 262 acquires multidimensional data such as the pixel value of each pixel included in an endoscopic image acquired by the image acquisition unit 261 and inputs the multidimensional data as input data to an input layer of the neural network of the operation selection model 265. The operation selection model 265 outputs five likelihoods respectively corresponding to the five operation details that can be selected as the operation detail of the endoscope 10 from an output layer of the neural network. The operation detail determination unit 262 can obtain an operation detail corresponding to one likelihood that is the highest among the five likelihoods included in the output data as the result of selecting the operation detail of the endoscope 10.

In the first exemplary embodiment, the operation detail determination unit 262 is formed so as to obtain a selection result indicating one operation detail selected from among five operation details including: operations for changing the direction of the distal end 12 to four directions orthogonal to the insertion axis of the insertion portion 11, respectively; and an operation for maintaining the direction of the distal end 12 to be the current direction, by inputting input data acquired from the endoscopic image acquired by the image acquisition unit 261 into the operation selection model 265 for processing.

The operation control unit 263 has a function of controlling the movement of the endoscope 10 based on the operation detail determined by the operation detail determination unit 262. The operation control unit 263 may set the operation amount in the determined operation detail based on at least one of insertion shape information output from the insertion shape detection apparatus 30 and external force information output from the external force information acquisition apparatus 40. The operation control unit 263 generates a movement control signal for performing movement control according to the operation detail determined by the operation detail determination unit 262 and the operation amount in the operation detail and outputs the movement control signal to the drive control unit 240.

The action of the first exemplary embodiment will now be explained. In the following, the explanation will be given using as an example a case in which control related to the insertion operation of the insertion portion 11 inserted into the intestinal tract of the large intestine from the anus. After connecting the parts of the endoscope system 1 and turning on the power, the user inserts the distal end 12 of the endoscope 10 into the anus of the subject. At this time, the user operates the input apparatus 50 so as to set an automatic insertion mode of the endoscope 10 to ON, which causes the processing apparatus 20 to perform an automatic operation function of the endoscope 10.

The light source unit 210 supplies illumination light to the endoscope 10, and the imaging unit 110 images the subject irradiated with the illumination light in a predetermined cycle and transmits the imaging signal to the processing apparatus 20. The image processing unit 220 generates an endoscopic image from the imaging signal and supplies the endoscopic image to the display control unit 250 and the image acquisition unit 261.

At this time, the coil drive signal generation unit 230 supplies a coil drive signal to the plurality of source coils 18, the receiving antenna 310 detects a magnetic field generated in each of the plurality of source coils 18, and the insertion shape information acquisition unit 320 generates insertion shape information of the insertion portion 11. The insertion shape information is supplied to the movement control unit 260 and the external force information acquisition apparatus 40. The external force information acquisition apparatus 40 generates external force information at each position of the plurality of source coils 18 from the insertion shape information and supplies the external force information to the movement control unit 260.

By inputting input data acquired from the endoscopic image acquired by the image acquisition unit 261 into the operation selection model 265 for processing, the operation detail determination unit 262 determines one operation detail from among the five operation details for the operation of the endoscope 10.

The operation control unit 263 generates a movement control signal for controlling the movement of the endoscope 10 based on the operation detail determined by the operation detail determination unit 262. The operation control unit 263 may perform a process for setting the operation amount in the determined operation detail based on at least one of insertion shape information output from the insertion shape detection apparatus 30 and external force information output from the external force information acquisition apparatus 40. The operation control unit 263 generates a movement control signal for performing movement control in accordance with the determined operation detail and the set operation amount and outputs the movement control signal to the drive control unit 240.

In the first exemplary embodiment, when the operation detail determined by the operation detail determination unit 262 is any one of the angle operation UPS, the angle operation DOS, the angle operation LES, and the angle operation RIS, the operation control unit 263 sets a bending angle CAS of the bending portion 13 as the operation amount in the operation detail. Then, the operation control unit 263 generates a movement control signal for executing control of bending the bending portion 13 by the bending angle CAS and outputs the movement control signal to the drive control unit 240. In addition to the control of bending the bending portion 13, the operation control unit 263 may set a rotation angle RAS of the insertion portion 11 and generate a movement control signal for executing control of rotating the insertion portion 11 by the rotation angle RAS.

On the other hand, the operation control unit 263 sets a moving amount MAS of the insertion portion 11 as the operation amount in the operation detail when the operation detail determined by the operation detail determination unit 262 is the angle maintenance operation AMS. Then, the operation control unit 263 generates a movement control signal for executing both control of fixing the bending angle of the bending portion 13 to the current bending angle and control of advancing the insertion portion 11 by the moving amount MAS and outputs the movement control signal to the drive control unit 240. The moving amount MAS is preferably set as a value within a range that allows the insertion portion 11 inserted into the intestinal tract to be safely advanced.

In the first exemplary embodiment, the operation control unit 263 sets the operation amount based on at least one of the insertion shape information output from the insertion shape detection apparatus 30 and the external force information output from the external force information acquisition apparatus 40. Alternatively, the operation control unit 263 may read a set value stored in advance in the storage medium 24 so as to set the operation amount.

When the user confirms that the observation has ended based on an endoscopic image displayed on the display apparatus 60, the user operates the input apparatus 50 so as to turn off the automatic insertion mode of the endoscope 10. This causes the processing apparatus 20 to stop the execution of the automatic operation function of the endoscope 10.

According to the first exemplary embodiment above, based on an endoscope image, the operation detail determination unit 262 can select an operation detail that is the same as an operation detail highly likely to be selected by a knowledgeable person from among the predetermined plural number of operation details for the operation of the endoscope 10. Further, according to the first exemplary embodiment, the operation control unit 263 can set the operation amount in the selected operation detail and generate a movement control signal for performing movement control on the endoscope 10. Therefore, according to the first exemplary embodiment, the operation detail of the endoscope 10 can be easily determined by using an operation selection model 265, which is a learned model.

In The first exemplary embodiment, the operation detail determination unit 262 may use an operation selection model different from operation selection models 265 for outputting the likelihood of each of the five operation details and determine the operation detail. For example, this operation selection model may be a learned model configured to output the likelihood of each of the four operation details: the angle operation UPS; the angle operation DOS; the angle operation LES; and the angle operation RIS. In this case, the operation control unit 263 may generate a movement control signal for performing control of bending the bending portion 13 according to the operation detail determined by the operation detail determination unit 262 and output the movement control signal to the drive control unit 240.

At this time, the operation control unit 263 may generate a movement control signal for advancing or retracting the insertion portion 11 based on at least one of the insertion shape information output from the insertion shape detection apparatus 30 and the external force information output from the external force information acquisition apparatus 40.

In the second to seventh exemplary embodiments in the following, variations of the operation selection model 265 will be explained, and explanations that are the same as those in the first embodiment will be omitted as appropriate.

Second Exemplary Embodiment

An operation selection model 265 according to the second exemplary embodiment is a learned model generated through the learning of each coupling coefficient (weight) in CNN corresponding to a multilayer neural network including an input layer, one or more convolutional layers, an output layer by a learning method such as deep learning. In the generation of an operation selection model 265 according to the second exemplary embodiment, machine learning using training data that includes an image for learning, which is an endoscopic image of the inside of an intestine or a colon model imaged by an endoscope in the past, and a label indicating which of nine operation details is most suitable for a situation shown by the image for learning.

The nine operation details include, for example, an angle operation UPS, an angle operation DOS, an angle operation LES, an angle operation RIS, an angle maintenance operation AMS, an angle operation URS for pointing the distal end 12 in an upper right direction by bending the bending portion 13, an angle operation ULS for pointing the distal end 12 in an upper left direction by bending the bending portion 13, an angle operation DLS for pointing the distal end 12 in a lower left direction by bending the bending portion 13, and an angle operation DRS for pointing the distal end 12 in a lower right direction by bending the bending portion 13.

In all the exemplary embodiments, an upper right direction of the distal end 12 is set as a direction orthogonal to the insertion axis of the insertion portion 11 and is also set as a direction located between an upward direction and a rightward direction of the distal end 12. Further, an upper left direction of the distal end 12 is set as a direction orthogonal to the insertion axis of the insertion portion 11 and is also set as a direction located between an upward direction and a leftward direction of the distal end 12. Further, a lower left direction of the distal end 12 is set as a direction orthogonal to the insertion axis of the insertion portion 11 and is also set as a direction located between a downward direction and a leftward direction of the distal end 12. Further, a lower right direction of the distal end 12 is set as a direction orthogonal to the insertion axis of the insertion portion 11 and is also set as a direction located between a downward direction and a rightward direction of the distal end 12.

At the time of generating the training data, a knowledgeable person looks at an image for learning, subjectively selects one operation detail that is most likely to be performed in a situation shown in the image for learning from among the nine operation details described above, and assigns a label of the selected operation detail to the image for learning. This label assigning task is performed on a large number of past endoscopic images, thereby generating the training data.

Figure 9:
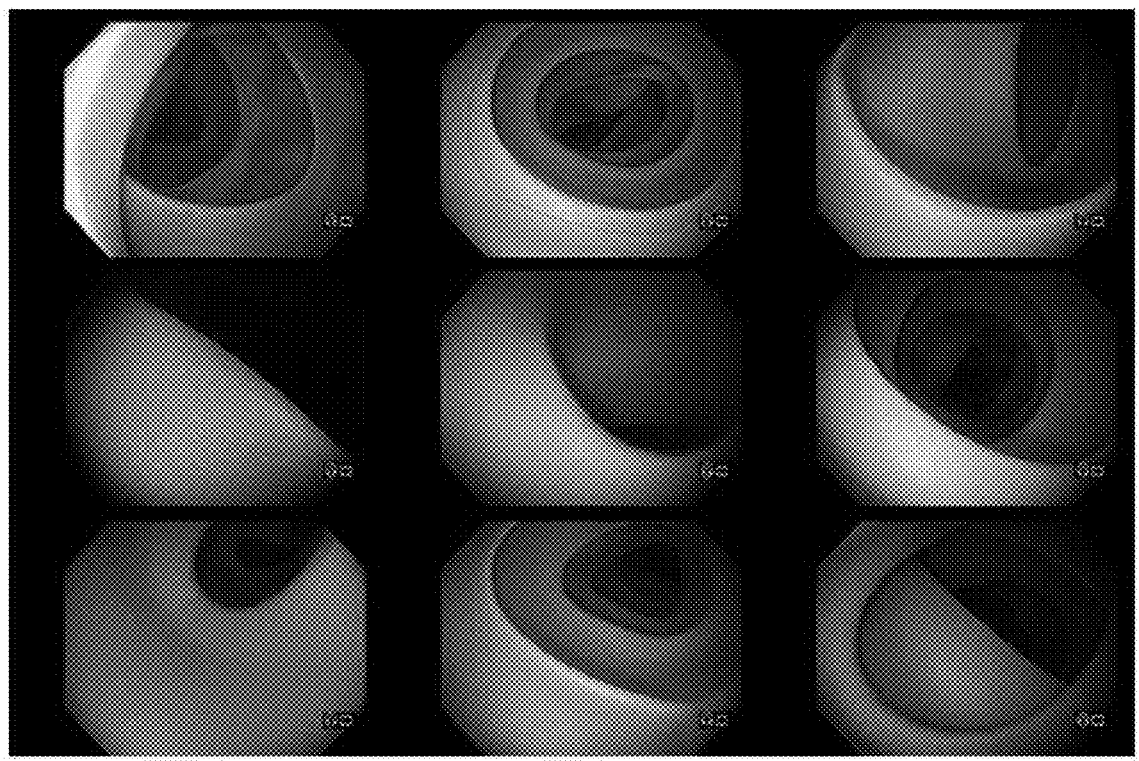
FIG. 9 shows an example of a training data set.

An example of training data including an image for learning and a label is shown below. FIG. 9 shows an example of the training data set. To all images for learning shown in FIG. 9, "angle operation URS label" indicating an angle operation in an upper right direction is assigned. The images for learning shown in FIG. 9 are images for which it has been decided that the bending portion 13 should be bent in an upper right direction as an endoscope operation to be performed next.

Figure 10:
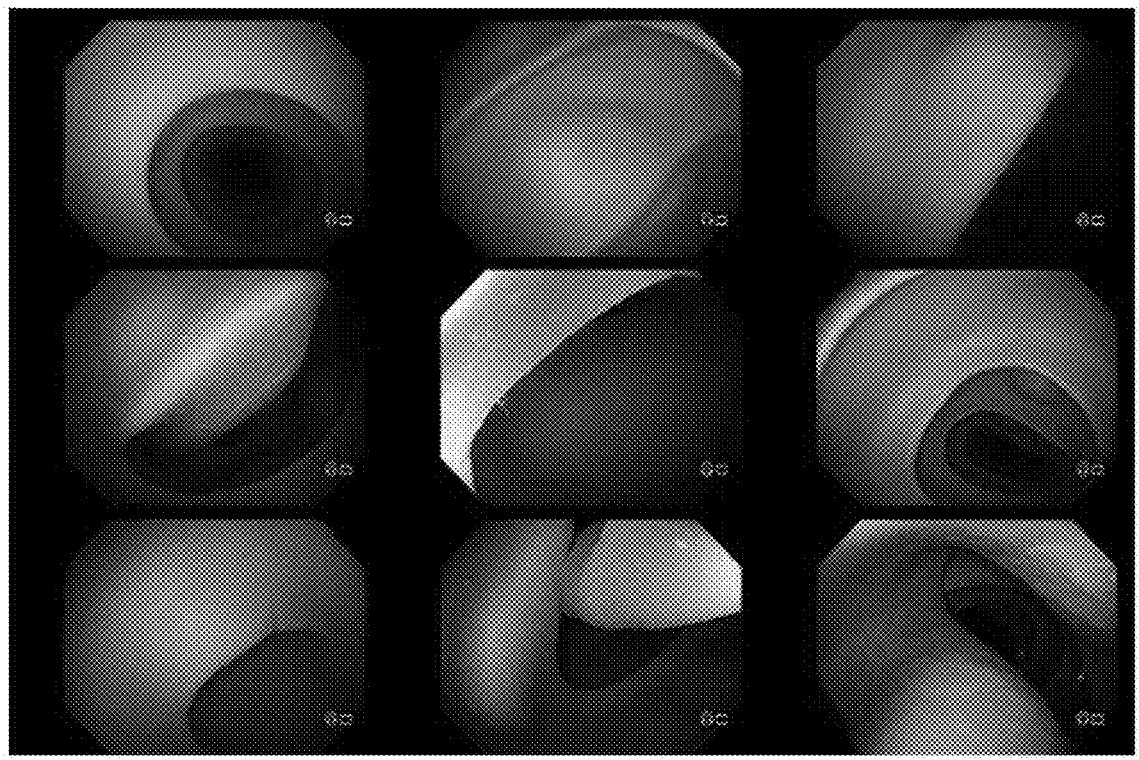
FIG. 10 shows an example of a training data set.

FIG. 10 shows another example of the training data set. To all images for learning shown in FIG. 10, "angle operation DRS label" indicating an angle operation in a lower right direction is being assigned. The images for learning shown in FIG. 10 are images for which it has been decided that the bending portion 13 should be bent in a lower right direction as an endoscope operation to be performed next.

Figure 11:
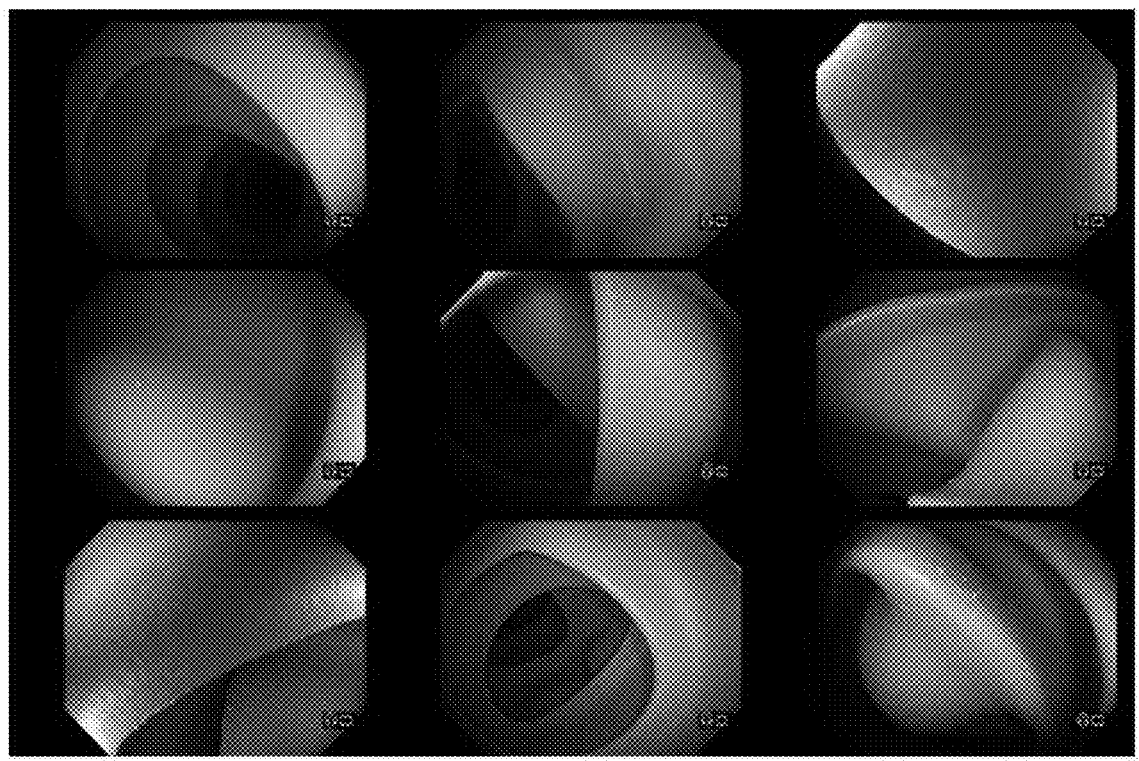
FIG. 11 shows an example of a training data set.

FIG. 11 shows another example of the training data set. To all images for learning shown in FIG. 11, "angle operation DLS label" indicating an angle operation in a lower left direction is being assigned. The images for learning shown in FIG. 11 are images for which it has been decided that the bending portion 13 should be bent in a lower left direction as an endoscope operation to be performed next.

Figure 12:
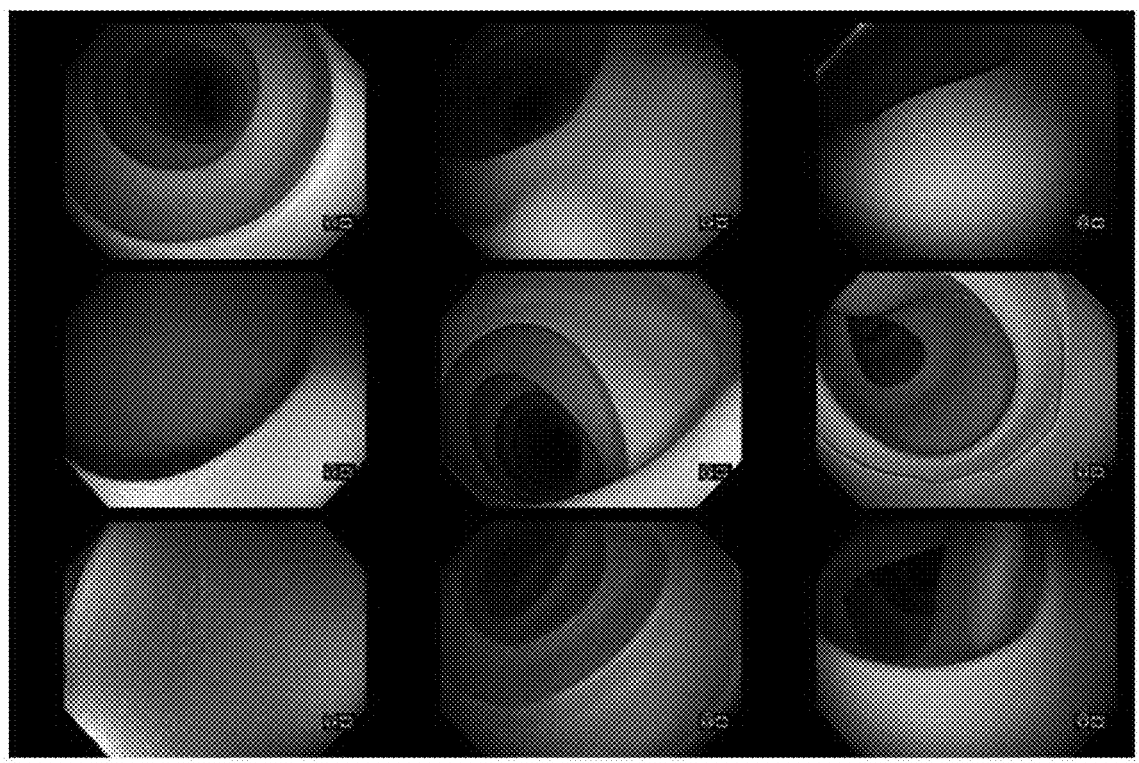
FIG. 12 shows an example of a training data set.

FIG. 12 shows another example of the training data set. To all images for learning shown in FIG. 12, "angle operation ULS label" indicating an angle operation in an upper left direction is being assigned. The images for learning shown in FIG. 12 are images for which it has been decided that the bending portion 13 should be bent in an upper left direction as an endoscope operation to be performed next. The operation selection model 265 according to the second exemplary embodiment is generated by machine learning using at least the training data sets shown in FIGS. 5 to 12.

The operation detail determination unit 262 determines one or more operation details by inputting input data acquired from an endoscopic image acquired in the image acquisition unit 261 to one or more into operation selection models 265 generated by machine learning using, as training data, an image for learning and a label indicating an operation detail for an endoscope that has imaged the image for learning. More specifically, the operation detail determination unit 262 acquires multidimensional data such as the pixel value of each pixel included in an endoscopic image acquired by the image acquisition unit 261 and inputs the multidimensional data as input data to an input layer of the neural network of the operation selection model 265. The operation selection model 265 according to the second exemplary embodiment outputs nine likelihoods respectively corresponding to the nine operation details that can be selected as the operation detail of the endoscope 10 from an output layer of the neural network. The operation detail determination unit 262 can obtain an operation detail corresponding to one likelihood that is the highest among the nine likelihoods included in the output data as the result of selecting the operation detail of the endoscope 10.

In the second exemplary embodiment, the operation detail determination unit 262 is formed so as to obtain a selection result indicating one operation detail selected from among nine operation details including: operations for changing the direction of the distal end 12 to eight directions orthogonal to the insertion axis of the insertion portion 11, respectively; and an operation for maintaining the direction of the distal end 12 to be the current direction, by inputting input data acquired from the endoscopic image acquired by the image acquisition unit 261 into the operation selection model 265 for processing.

The operation control unit 263 has a function of controlling the movement of the endoscope 10 based on the operation detail determined by the operation detail determination unit 262. The operation control unit 263 may set the operation amount in the determined operation detail based on at least one of insertion shape information output from the insertion shape detection apparatus 30 and external force information output from the external force information acquisition apparatus 40. The operation control unit 263 generates a movement control signal for performing movement control according to the operation detail determined by the operation detail determination unit 262 and the operation amount in the operation detail and outputs the movement control signal to the drive control unit 240.

The action of the second exemplary embodiment will now be explained. By inputting input data acquired from the endoscopic image acquired by the image acquisition unit 261 into the operation selection model 265 according to the second exemplary embodiment for processing, the operation detail determination unit 262 determines one operation detail from among the nine operation details for the operation of the endoscope 10.

The operation control unit 263 generates a movement control signal for controlling the movement of the endoscope 10 based on the operation detail determined by the operation detail determination unit 262. The operation control unit 263 may perform a process for setting the operation amount in the determined operation detail based on at least one of insertion shape information output from the insertion shape detection apparatus 30 and external force information output from the external force information acquisition apparatus 40. The operation control unit 263 generates a movement control signal for performing movement control in accordance with the determined operation detail and the set operation amount and outputs the movement control signal to the drive control unit 240.

In the second exemplary embodiment, when the operation detail determined by the operation detail determination unit 262 is any one of the angle operation UPS, the angle operation DOS, the angle operation LES, the angle operation RIS, the angle operation URS, the angle operation ULS, the angle operation DLS, and the angle operation DRS, the operation control unit 263 sets a bending angle CBS of the bending portion 13 as the operation amount in the operation detail. Then, the operation control unit 263 generates a movement control signal for executing control of bending the bending portion 13 by the bending angle CBS and outputs the movement control signal to the drive control unit 240. In addition to the control of bending the bending portion 13, the operation control unit 263 may set a rotation angle RBS of the insertion portion 11 and generate a movement control signal for executing control of rotating the insertion portion 11 by the rotation angle RBS.

On the other hand, the operation control unit 263 sets a moving amount MBS of the insertion portion 11 as the operation amount in the operation detail when the operation detail determined by the operation detail determination unit 262 is the angle maintenance operation AMS. Then, the operation control unit 263 generates a movement control signal for executing both control of fixing the bending angle of the bending portion 13 to the current bending angle and control of advancing the insertion portion 11 by the moving amount MBS and outputs the movement control signal to the drive control unit 240. The moving amount MBS is preferably set as a value within a range that allows the insertion portion 11 inserted into the intestinal tract to be safely advanced.

In the second exemplary embodiment, the operation control unit 263 sets the operation amount based on at least one of the insertion shape information output from the insertion shape detection apparatus 30 and the external force information output from the external force information acquisition apparatus 40. Alternatively, the operation control unit 263 may read a set value stored in advance in the storage medium 24 so as to set the operation amount.

According to the second exemplary embodiment above, based on an endoscope image, the operation detail determination unit 262 can select an operation detail that is the same as an operation detail highly likely to be selected by a knowledgeable person from among the predetermined plural number of operation details for the operation of the endoscope 10. Further, according to the second exemplary embodiment, the operation control unit 263 can set the operation amount in the selected operation detail and generate a movement control signal for performing movement control on the endoscope 10. Therefore, according to the second exemplary embodiment, the operation detail of the endoscope 10 can be easily determined by using an operation selection model 265, which is a learned model.

In the second exemplary embodiment, the operation detail determination unit 262 may use an operation selection model different from operation selection models 265 for outputting the likelihood of each of the nine operation details and determine the operation detail. For example, this operation selection model may be a learned model configured to output the likelihood of each of the eight operation details: the angle operation UPS; the angle operation DOS; the angle operation LES; the angle operation RIS; the angle operation URS; the angle operation ULS; the angle operation DLS; and the angle operation DRS. In this case, the operation control unit 263 may generate a movement control signal for performing control of bending the bending portion 13 according to the operation detail determined by the operation detail determination unit 262 and output the movement control signal to the drive control unit 240.

At this time, the operation control unit 263 may generate a movement control signal for advancing or retracting the insertion portion 11 based on at least one of the insertion shape information output from the insertion shape detection apparatus 30 and the external force information output from the external force information acquisition apparatus 40.

Third Exemplary Embodiment

An operation selection model 265 according to the third exemplary embodiment is a learned model generated through the learning of each coupling coefficient (weight) in CNN corresponding to a multilayer neural network including an input layer, one or more convolutional layers, an output layer by a learning method such as deep learning. In the generation of an operation selection model 265 according to the third exemplary embodiment, machine learning using training data that includes an image for learning, which is an endoscopic image of the inside of an intestine or a colon model imaged by an endoscope in the past, and a label indicating which of ten operation details is most suitable for a situation shown by the image for learning.

The ten operation details include an angle operation UPS, an angle operation DOS, an angle operation LES, an angle operation RIS, an angle operation URS, an angle operation ULS, an angle operation DLS, an angle operation DRS, a push operation PSS for advancing the distal end 12, and a pull operation PLS for retracting the distal end 12.

At the time of generating the training data, a knowledgeable person looks at the image for learning, subjectively selects one operation detail that is most likely to be performed in a situation shown in the image for learning from among the ten operation details described above, and assigns a label of the selected operation detail to the image for learning. This label assigning task is performed on a large number of past endoscopic images, thereby generating the training data.

Figure 13:
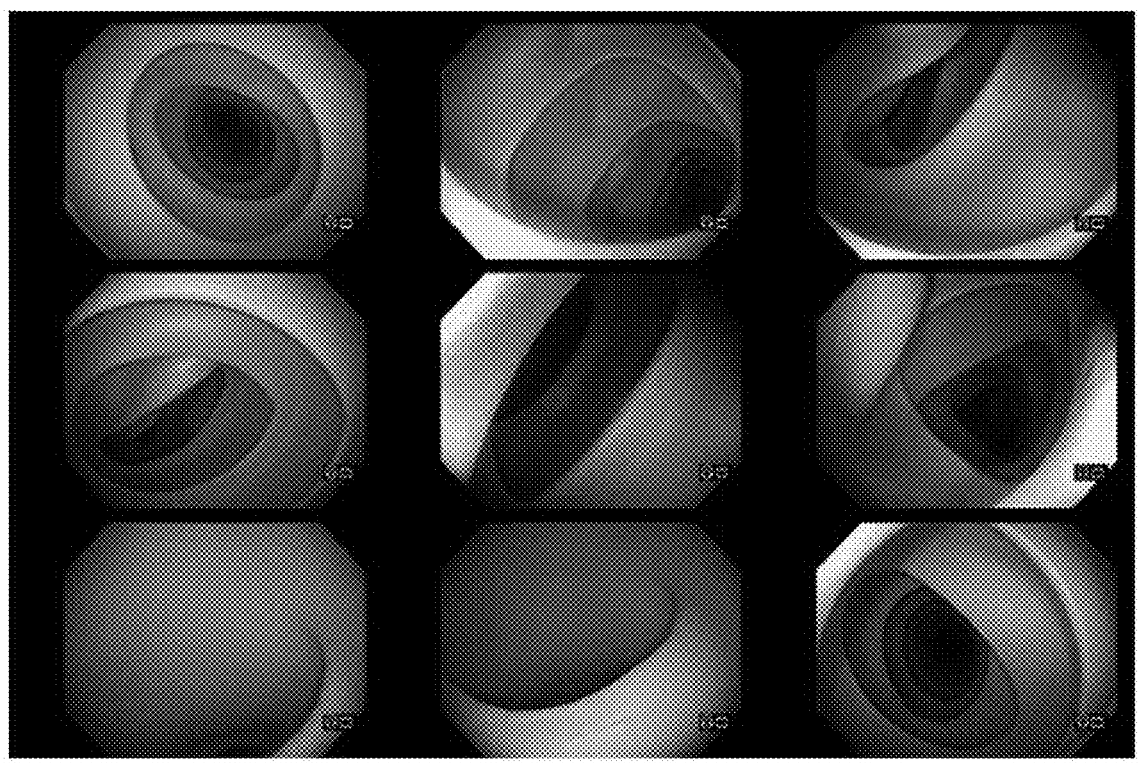
FIG. 13 shows an example of a training data set.

An example of training data including an image for learning and a label is shown below. FIG. 13 shows an example of a training data set. To all images for learning shown in FIG. 13, "push operation PSS label" indicating a push operation is assigned. The images for learning shown in FIG. 13 are images for which it has been decided that the distal end 12 should be advanced as an endoscope operation to be performed next.

Figure 14:
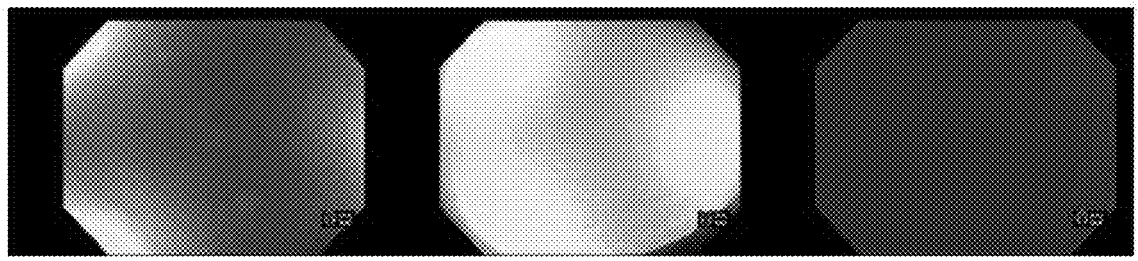
FIG. 14 shows an example of a training data set.

FIG. 14 shows another example of the training data set. To all images for learning shown in FIG. 14, "pull operation PLS label" indicating a pull operation is being assigned. The images for learning shown in FIG. 14 are images for which it has been decided that the distal end 12 should be retracted as an endoscope operation to be performed next. A typical example of a situation where a pull operation is required is a situation such as a situation where the distal end 12 is excessively close to the mucosal surface of the colon and a situation where the distal end 12 is in contact with the mucosal surface, which is commonly referred to as "red out" by endoscopists. The operation selection model 265 according to the third exemplary embodiment is generated by machine learning using at least the training data sets shown in FIGS. 5 to 14.

The operation detail determination unit 262 determines one or more operation details by inputting input data acquired from an endoscopic image acquired in the image acquisition unit 261 to one or more into operation selection models 265 generated by machine learning using, as training data, an image for learning and a label indicating an operation detail for an endoscope that has imaged the image for learning. More specifically, the operation detail determination unit 262 acquires multidimensional data such as the pixel value of each pixel included in an endoscopic image acquired by the image acquisition unit 261 and inputs the multidimensional data as input data to an input layer of the neural network of the operation selection model 265. The operation selection model 265 according to the third exemplary embodiment outputs ten likelihoods respectively corresponding to the ten operation details that can be selected as the operation detail of the endoscope 10 from an output layer of the neural network. The operation detail determination unit 262 can obtain an operation detail corresponding to one likelihood that is the highest among the ten likelihoods included in the output data as the result of selecting the operation detail of the endoscope 10.

In the third exemplary embodiment, the operation detail determination unit 262 is formed so as to obtain a selection result indicating one operation detail selected from among ten operation details including: operations for changing the direction the distal end 12 to eight directions orthogonal to the insertion axis of the insertion portion 11, respectively; and an operation for advancing or retracting the distal end 12, by inputting input data acquired from the endoscopic image acquired by the image acquisition unit 261 into the operation selection model 265 for processing.

The operation control unit 263 has a function of controlling the movement of the endoscope 10 based on the operation detail determined by the operation detail determination unit 262. The operation control unit 263 may set the operation amount in the determined operation detail based on at least one of insertion shape information output from the insertion shape detection apparatus 30 and external force information output from the external force information acquisition apparatus 40. The operation control unit 263 generates a movement control signal for performing movement control according to the operation detail determined by the operation detail determination unit 262 and the operation amount in the operation detail and outputs the movement control signal to the drive control unit 240.

The action of the third exemplary embodiment will now be explained. By inputting input data acquired from the endoscopic image acquired by the image acquisition unit 261 into the operation selection model 265 according to the third exemplary embodiment for processing, the operation detail determination unit 262 determines one operation detail from among the ten operation details for the operation of the endoscope 10.

The operation control unit 263 generates a movement control signal for controlling the movement of the endoscope 10 based on the operation detail determined by the operation detail determination unit 262. The operation control unit 263 may perform a process for setting the operation amount in the determined operation detail based on at least one of insertion shape information output from the insertion shape detection apparatus 30 and external force information output from the external force information acquisition apparatus 40. The operation control unit 263 generates a movement control signal for performing movement control in accordance with the determined operation detail and the set operation amount and outputs the movement control signal to the drive control unit 240.

In the third exemplary embodiment, when the operation detail determined by the operation detail determination unit 262 is any one of the angle operation UPS, the angle operation DOS, the angle operation LES, the angle operation RIS, the angle operation URS, the angle operation ULS, the angle operation DLS, and the angle operation DRS, the operation control unit 263 sets a bending angle CCS of the bending portion 13 as the operation amount in the operation detail. Then, the operation control unit 263 generates a movement control signal for executing control of bending the bending portion 13 by the bending angle CCS and outputs the movement control signal to the drive control unit 240. In addition to the control of bending the bending portion 13, the operation control unit 263 may set a rotation angle RCS of the insertion portion 11 and generate a movement control signal for executing control of rotating the insertion portion 11 by the rotation angle RCS.

The operation control unit 263 sets a moving amount MCS of the insertion portion 11 as the operation amount in the operation detail when the operation detail determined by the operation detail determination unit 262 is the push operation PSS. Then, the operation control unit 263 generates a movement control signal for executing control of advancing the insertion portion 11 by the moving amount MCS and outputs the movement control signal to the drive control unit 240. The moving amount MCS is preferably set as a value within a range that allows the insertion portion 11 inserted into the intestinal tract to be safely advanced.

The operation control unit 263 sets a moving amount MDS of the insertion portion 11 as the operation amount in the operation detail when the operation detail determined by the operation detail determination unit 262 is the pull operation PLS. Then, the operation control unit 263 generates a movement control signal for executing control of retracting the insertion portion 11 by the moving amount MDS and outputs the movement control signal to the drive control unit 240. The moving amount MDS is preferably set as a value within a range that allows the insertion portion 11 inserted into the intestinal tract to be safely retracted.

In the third exemplary embodiment, the operation control unit 263 sets the operation amount based on at least one of the insertion shape information output from the insertion shape detection apparatus 30 and the external force information output from the external force information acquisition apparatus 40. Alternatively, the operation control unit 263 may read a set value stored in advance in the storage medium 24 so as to set the operation amount.

According to the third exemplary embodiment above, based on an endoscope image, the operation detail determination unit 262 can select an operation detail that is the same as an operation detail highly likely to be selected by a knowledgeable person from among the predetermined plural number of operation details for the operation of the endoscope 10. Further, according to the third exemplary embodiment, the operation control unit 263 can set the operation amount in the selected operation detail and generate a movement control signal for performing movement control on the endoscope 10. Therefore, according to the third exemplary embodiment, the operation detail of the endoscope 10 can be easily determined by using an operation selection model 265, which is a learned model.

According to the operation detail determination unit 262 and the operation control unit 263 according to the third exemplary embodiment, for example, when a part of the lumen in the field of view of the imaging unit 110 is blocked by a fold located in front of the lumen, an insertion operation can be achieved that causes the distal end 12 to approach the lumen while changing the position and direction of the distal end 12 to avoid contact with the fold. According to the operation detail determination unit 262 and the operation control unit 263, for example, when the lumen in the field of view of the imaging unit 110 is hidden behind the intestinal wall, an insertion operation can be achieved that causes the distal end 12 to approach the lumen after moving the distal end 12 around the side of the intestinal wall.

Fourth Exemplary Embodiment

An operation selection model 265 according to the fourth exemplary embodiment is a learned model generated through the learning of each coupling coefficient (weight) in CNN corresponding to a multilayer neural network including an input layer, one or more convolutional layers, an output layer by a learning method such as deep learning. In the generation of an operation selection model 265 according to the fourth exemplary embodiment, machine learning using training data that includes an image for learning, which is an endoscopic image of the inside of an intestine or a colon model imaged by an endoscope in the past, and a label indicating which of twelve operation details is most suitable for a situation shown by the image for learning.

The twelve operation details include an angle operation UPS, an angle operation DOS, an angle operation LES, an angle operation RIS, an angle operation URS, an angle operation ULS, an angle operation DLS, an angle operation DRS, a push operation PSS, a pull operation PLS, an angle maintenance operation AMS, and a search operation SES for pointing the distal end 12 in a plurality of directions to search for the lumen.

At the time of generating the training data, a knowledgeable person looks at the image for learning, subjectively selects one operation detail that is most likely to be performed in a situation shown in the image for learning from among the twelve operation details described above, and assigns a label of the selected operation detail to the image for learning. This label assigning task is performed on a large number of past endoscopic images, thereby generating the training data.

Figure 15:
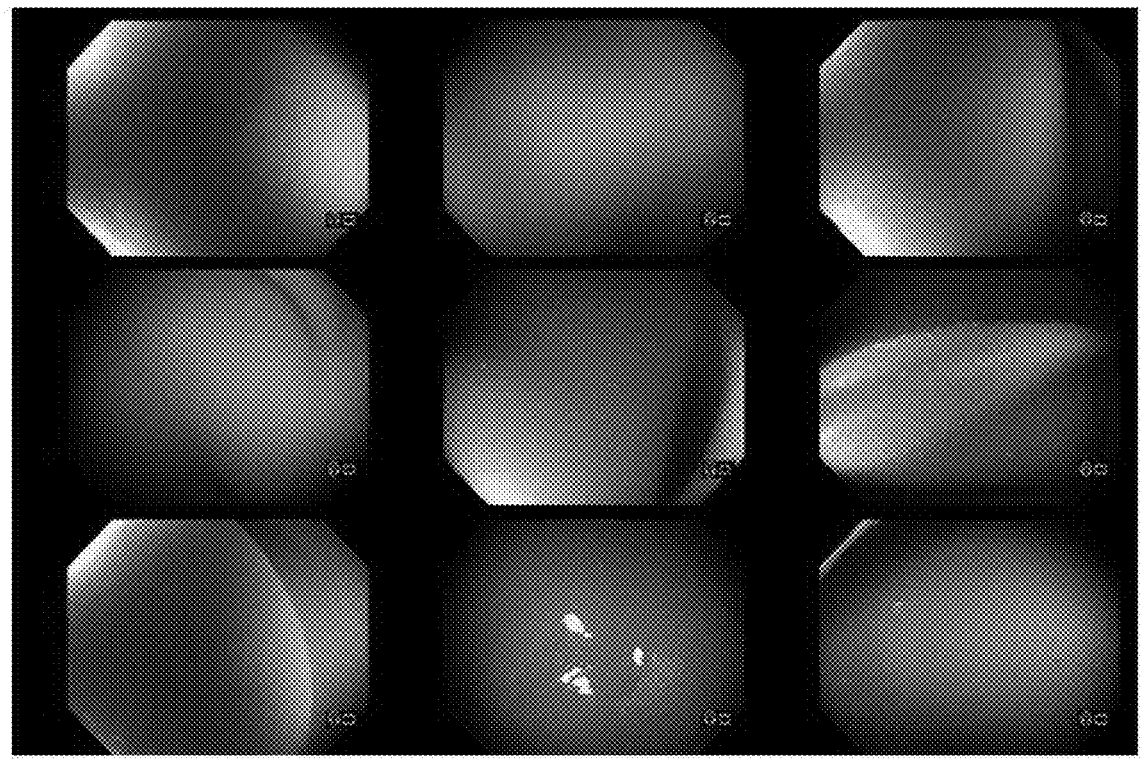
FIG. 15 shows an example of a training data set.

An example of training data including an image for learning and a label is shown below. FIG. 15 shows an example of a training data set. To all images for learning shown in FIG. 15, "search operation SES label" indicating a search operation is assigned. The images for learning shown in FIG. 15 are images for which it has been decided that the bending portion 13 should be bent in a plurality of directions to image several images as an endoscope operation to be performed next. The operation selection model 265 according to the fourth exemplary embodiment is generated by machine learning using at least the training data sets shown in FIGS. 5 to 15.

The operation detail determination unit 262 determines one or more operation details by inputting input data acquired from an endoscopic image acquired in the image acquisition unit 261 to one or more into operation selection models 265 generated by machine learning using, as training data, an image for learning and a label indicating an operation detail for an endoscope that has imaged the image for learning. More specifically, the operation detail determination unit 262 acquires multidimensional data such as the pixel value of each pixel included in an endoscopic image acquired by the image acquisition unit 261 and inputs the multidimensional data as input data to an input layer of the neural network of the operation selection model 265. The operation selection model 265 according to the fourth exemplary embodiment outputs twelve likelihoods respectively corresponding to the twelve operation details that can be selected as the operation detail of the endoscope 10 from an output layer of the neural network. The operation detail determination unit 262 can obtain an operation detail corresponding to one likelihood that is the highest among the twelve likelihoods included in the output data as the result of selecting the operation detail of the endoscope 10.

In the fourth exemplary embodiment, the operation detail determination unit 262 is formed so as to obtain a selection result indicating one operation detail selected from among twelve operation details including: operations for changing the direction the distal end 12 to eight directions orthogonal to the insertion axis of the insertion portion 11, respectively; an operation for advancing or retracting the distal end 12; an operation for maintaining the direction of the distal end 12 to be the current direction; and an operation for searching for a lumen near the distal end 12, by inputting input data acquired from the endoscopic image acquired by the image acquisition unit 261 into the operation selection model 265 for processing.

The operation control unit 263 has a function of controlling the movement of the endoscope 10 based on the operation detail determined by the operation detail determination unit 262. At this time, the operation control unit 263 may set the operation amount in the determined operation detail based on at least one of insertion shape information output from the insertion shape detection apparatus 30 and external force information output from the external force information acquisition apparatus 40. The operation control unit 263 generates a movement control signal for performing movement control according to the operation detail determined by the operation detail determination unit 262 and the operation amount in the operation detail and outputs the movement control signal to the drive control unit 240.

The action of the fourth exemplary embodiment will now be explained. By inputting input data acquired from the endoscopic image acquired by the image acquisition unit 261 into the operation selection model 265 according to the fourth exemplary embodiment for processing, the operation detail determination unit 262 determines one operation detail from among the twelve operation details for the operation of the endoscope 10.

The operation control unit 263 generates a movement control signal for controlling the movement of the endoscope 10 based on the operation detail determined by the operation detail determination unit 262. The operation control unit 263 may perform a process for setting the operation amount in the determined operation detail based on at least one of insertion shape information output from the insertion shape detection apparatus 30 and external force information output from the external force information acquisition apparatus 40. The operation control unit 263 generates a movement control signal for performing movement control in accordance with the determined operation detail and the set operation amount and outputs the movement control signal to the drive control unit 240.

In the fourth exemplary embodiment, when the operation detail determined by the operation detail determination unit 262 is any one of the angle operation UPS, the angle operation DOS, the angle operation LES, the angle operation RIS, the angle operation URS, the angle operation ULS, the angle operation DLS, and the angle operation DRS, the operation control unit 263 sets a bending angle CDS of the bending portion 13 as the operation amount in the operation detail. Then, the operation control unit 263 generates a movement control signal for executing control of bending the bending portion 13 by the bending angle CDS and outputs the movement control signal to the drive control unit 240. In addition to the control of bending the bending portion 13, the operation control unit 263 may set a rotation angle RDS of the insertion portion 11 and generate a movement control signal for executing control of rotating the insertion portion 11 by the rotation angle RDS.

The operation control unit 263 sets a moving amount MES of the insertion portion 11 as the operation amount in the operation detail when the operation detail determined by the operation detail determination unit 262 is the push operation PSS. Then, the operation control unit 263 generates a movement control signal for executing control of advancing the insertion portion 11 by the moving amount MES and outputs the movement control signal to the drive control unit 240. The moving amount MES is preferably set as a value within a range that allows the insertion portion 11 inserted into the intestinal tract to be safely advanced.

The operation control unit 263 sets a moving amount MFS of the insertion portion 11 as the operation amount in the operation detail when the operation detail determined by the operation detail determination unit 262 is the pull operation PLS. Then, the operation control unit 263 generates a movement control signal for executing control of retracting the insertion portion 11 by the moving amount MFS and outputs the movement control signal to the drive control unit 240. The moving amount MFS is preferably set as a value within a range that allows the insertion portion 11 inserted into the intestinal tract to be safely retracted.

The operation control unit 263 generates a movement control signal for executing control of maintaining the bending angle of the bending portion 13 to be the current bending angle when the operation detail determined by the operation detail determination unit 262 is the angle maintenance operation AMS and outputs the movement control signal to the drive control unit 240.

The operation control unit 263 sets a moving amount MGS of the insertion portion 11 as the operation amount in the operation detail when the operation detail determined by the operation detail determination unit 262 is the search operation SES. Then, the operation control unit 263 generates a movement control signal for executing control of pointing the distal end 12 in a plurality of directions after retracting the insertion portion 11 by the moving amount MGS and outputs the movement control signal to the drive control unit 240. At this time, the operation control unit 263 may generate a movement control signal for executing control of pointing the distal end 12 in four or eight directions. In a process related to the search operation SES, a process of pointing the distal end 12 in a plurality of directions and finding the lumen in endoscopic images imaged in the respective directions is performed.

In the fourth exemplary embodiment, the operation control unit 263 sets the operation amount based on at least one of the insertion shape information output from the insertion shape detection apparatus 30 and the external force information output from the external force information acquisition apparatus 40. Alternatively, the operation control unit 263 may read a set value stored in advance in the storage medium 24 so as to set the operation amount.

According to the fourth exemplary embodiment above, based on an endoscope image, the operation detail determination unit 262 can select an operation detail that is the same as an operation detail highly likely to be selected by a knowledgeable person from among twelve operation details for the operation of the endoscope 10. Further, according to the fourth exemplary embodiment, the operation control unit 263 can set the operation amount in the selected operation detail and generate a movement control signal for performing movement control on the endoscope 10. Therefore, according to the fourth exemplary embodiment, the operation detail of the endoscope 10 can be easily determined by using an operation selection model 265, which is a learned model.

In the first through fourth exemplary embodiments, it has been explained that training data may include a label indicating an angle operation and a label indicating a push operation. The training data may further include a label indicating a twist operation, which is an operation of twisting the insertion portion 11 around the insertion axis, more specifically, a label indicating a leftward twisting operation and/or a label indicating a rightward twisting operation.

Fifth Exemplary Embodiment

In the first through fourth exemplary embodiments, an operation selection model 265 is generated through machine learning using training data including an endoscopic image and a label indicating an operation detail. In the fifth exemplary embodiment, a label is set for the combination of an operation detail and an operation amount in the operation detail, and an operation selection model 265 is generated through machine learning.

An operation selection model 265 according to the fifth exemplary embodiment is a learned model generated through the learning of each coupling coefficient (weight) in CNN corresponding to a multilayer neural network including an input layer, one or more convolutional layers, an output layer by a learning method such as deep learning. In the generation of an operation selection model 265 according to the fifth exemplary embodiment, machine learning using training data that includes an image for learning, which is an endoscopic image of the inside of an intestine or a colon model imaged by an endoscope in the past, and a label indicating which of twelve operation details is most suitable for a situation shown by the image for learning.

The twelve operation details include an angle operation UPS, an angle operation DOS, an angle operation LES, an angle operation RIS, an angle operation URS, an angle operation ULS, an angle operation DLS, an angle operation DRS, a push operation PSS_AL in which a moving amount is relatively large, a push operation PSS_AS in which a moving amount is relatively small, a pull operation PLS, and a search operation SES.

At the time of generating the training data, a knowledgeable person looks at the image for learning, subjectively selects one operation detail that is most likely to be performed in a situation shown in the image for learning from among the twelve operation details described above, and assigns a label of the selected operation detail to the image for learning. This label assigning task is performed on a large number of past endoscopic images, thereby generating the training data.

Figure 16A:
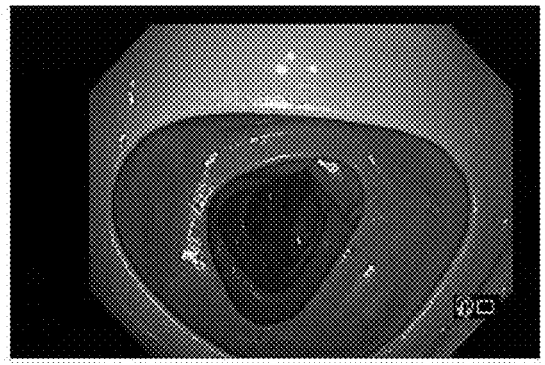
FIGS. 16A and 16B are diagrams showing examples of images for learning.
Figure 16B:
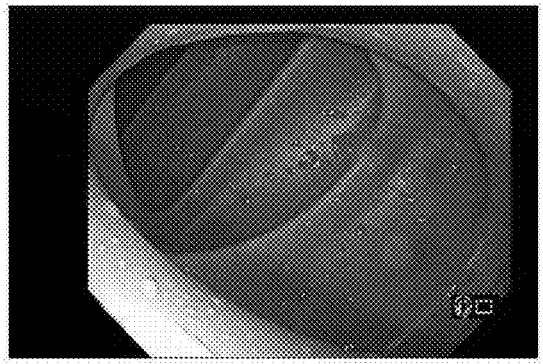

An example of training data including an image for learning and a label is shown below. FIG. 16A shows an image for learning of the large intestine being curved to a small extent, and FIG. 16B shows an image for learning of the large intestine being curved to a large extent. For all the images for learning shown in FIGS. 16A and 16B, a knowledgeable person also decides that the distal end 12 should be advanced as an endoscope operation to be performed next.

At this time, the knowledgeable person decides for the image for learning in FIG. 16A that the insertion portion 11 can be advanced for a relatively long distance. On the other hand, the knowledgeable person decides for the image for learning in FIG. 16B that the insertion portion 11 cannot be advanced over a long distance and is advanced only for a relatively short distance. Thus, "push operation PSS_AL label" indicating a push operation with a moving amount of 5 cm is assigned to the image for learning shown in FIG. 16A, and "push operation PSS_AS label" indicating a push operation with a moving amount of 2 cm is assigned to the image for learning shown in FIG. 16B.

In the third exemplary embodiment, "push operation PSS label" indicating a push operation is assigned to all the images for learning shown in FIG. 13. However, in the fifth exemplary embodiment, either one of "push operation PSS_AL label" and "push operation PSS_AS label" is assigned to the images for learning shown in FIG. 13. The operation selection model 265 according to the fifth exemplary embodiment is generated by machine learning using at least the training data sets shown in FIGS. 5 to 12 and FIGS. 14 to 16.

The operation detail determination unit 262 determines one or more operation details by inputting input data acquired from an endoscopic image acquired in the image acquisition unit 261 to one or more into operation selection models 265 generated by machine learning using, as training data, an image for learning and a label indicating an operation detail for an endoscope that has imaged the image for learning. More specifically, the operation detail determination unit 262 acquires multidimensional data such as the pixel value of each pixel included in an endoscopic image acquired by the image acquisition unit 261 and inputs the multidimensional data as input data to an input layer of the neural network of the operation selection model 265. The operation selection model 265 according to the fifth exemplary embodiment outputs twelve likelihoods respectively corresponding to the twelve operation details that can be selected as the operation detail of the endoscope 10 from an output layer of the neural network. The operation detail determination unit 262 can obtain an operation detail corresponding to one likelihood that is the highest among the twelve likelihoods included in the output data as the result of selecting the operation detail of the endoscope 10.

The action of the fifth exemplary embodiment will now be explained. By inputting input data acquired from the endoscopic image acquired by the image acquisition unit 261 into the operation selection model 265 according to the fifth exemplary embodiment for processing, the operation detail determination unit 262 determines one operation detail from among the twelve operation details for the operation of the endoscope 10.

The operation control unit 263 generates a movement control signal for executing control of advancing the insertion portion 11 just by 5 cm when the operation detail determined by the operation detail determination unit 262 is the push operation PSS_AL and outputs the movement control signal to the drive control unit 240. Thereby, the advancing and retracting control unit 241 generates an advancing and retracting control signal for advancing the insertion portion 11 by 5 cm and drives the advancing and retracting mechanism 141.

The operation control unit 263 generates a movement control signal for executing control of advancing the insertion portion 11 just by 2 cm when the operation detail determined by the operation detail determination unit 262 is the push operation PSS_AS and outputs the movement control signal to the drive control unit 240. Thereby, the advancing and retracting control unit 241 generates an advancing and retracting control signal for advancing the insertion portion 11 by 2 cm and drives the advancing and retracting mechanism 141.

As described above, a label is set for a combination of a push operation for the insertion portion 11 and a moving amount caused by the push operation and used for machine learning as training data in the fifth exemplary embodiment. With regard to the operation amount, push operations are classified into two classes. Alternatively, the push operations may be classified into three or more classes.

Further, a label may be set for a combination of not only a push operation but also an angle operation and a rotation angle due to the angle operation and used for machine learning as training data. As described, in the fifth exemplary embodiment, training data in which a label is set for the combination of an operation detail and an operation amount in the operation detail is used so as to generate an operation selection model 265. Thereby, the operation detail and operation amount of the endoscope 10 can be easily determined by using the operation selection model 265.

Sixth Exemplary Embodiment

In general, it is desirable for colonoscopy to be completed in a short time from the viewpoint of patient burden. Therefore, it is desirable to execute a prompt insertion operation and without waste under a safe situation. On the other hand, careful operations are required depending on the condition of the colon. In the sixth exemplary embodiment, a label is set for the combination of an operation detail and a movement speed in the operation detail, and an operation selection model 265 is generated through machine learning.

An operation selection model 265 according to the sixth exemplary embodiment is a learned model generated through the learning of each coupling coefficient (weight) in CNN corresponding to a multilayer neural network including an input layer, one or more convolutional layers, an output layer by a learning method such as deep learning. In the generation of an operation selection model 265 according to the sixth exemplary embodiment, machine learning using training data that includes an image for learning, which is an endoscopic image of the inside of an intestine or a colon model imaged by an endoscope in the past, and a label indicating which of twelve operation details is most suitable for a situation shown by the image for learning.

The twelve operation details include an angle operation UPS, an angle operation DOS, an angle operation LES, an angle operation RIS, an angle operation URS, an angle operation ULS, an angle operation DLS, an angle operation DRS, a push operation PSS_SH in which a moving speed is relatively high, a push operation PSS_SL in which a moving speed is relatively low, a pull operation PLS, and a search operation SES.

At the time of generating the training data, a knowledgeable person looks at the image for learning, subjectively selects one operation detail that is most likely to be performed in a situation shown in the image for learning from among the twelve operation details described above, and assigns a label of the selected operation detail to the image for learning. This label assigning task is performed on a large number of past endoscopic images, thereby generating the training data.

Figure 17A:
FIGS. 17A and 17B are diagrams showing examples of images for learning.
Figure 17B:
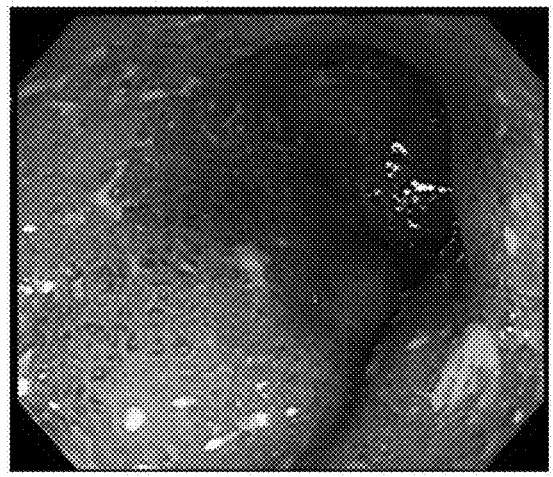

An example of training data including an image for learning and a label is shown below. FIG. 17A shows an image for learning of a part without abnormality, and FIG. 17B shows an image for learning of a part with an abnormality such as mucosal inflammation. For all the images for learning shown in FIGS. 17A and 17B, a knowledgeable person also decides that the distal end 12 should be advanced as an endoscope operation to be performed next.

At this time, the knowledgeable person decides for the image for learning in FIG. 17A that the insertion portion 11 may be advanced at a relatively high speed. On the other hand, the knowledgeable person decides for the image for learning in FIG. 17B that the insertion portion 11 needs to be advanced carefully and is advanced at a relatively low speed. Thus, "push operation PSS_SH label" indicating a push operation at a moving speed of 5 cm/sec is assigned to the image for learning shown in FIG. 17A, and "push operation PSS_SL label" indicating a push operation at a moving speed of 2 cm/sec is assigned to the image for learning shown in FIG. 17B.

In the third exemplary embodiment, "push operation PSS label" indicating a push operation is assigned to all the images for learning shown in FIG. 13. However, in the sixth exemplary embodiment, either one of "push operation PSS_SH label" and "push operation PSS_SL label" is assigned to the images for learning shown in FIG. 13. The operation selection model 265 according to the sixth exemplary embodiment is generated by machine learning using at least the training data sets shown in FIGS. 5 to 12, FIG. 14, FIG. 15, and FIG. 17.

The operation detail determination unit 262 determines one or more operation details by inputting input data acquired from an endoscopic image acquired in the image acquisition unit 261 to one or more into operation selection models 265 generated by machine learning using, as training data, an image for learning and a label indicating an operation detail for an endoscope that has imaged the image for learning. More specifically, the operation detail determination unit 262 acquires multidimensional data such as the pixel value of each pixel included in an endoscopic image acquired by the image acquisition unit 261 and inputs the multidimensional data as input data to an input layer of the neural network of the operation selection model 265. The operation selection model 265 according to the sixth exemplary embodiment outputs twelve likelihoods respectively corresponding to the twelve operation details that can be selected as the operation detail of the endoscope 10 from an output layer of the neural network. The operation detail determination unit 262 can obtain an operation detail corresponding to one likelihood that is the highest among the twelve likelihoods included in the output data as the result of selecting the operation detail of the endoscope 10.

The action of the sixth exemplary embodiment will now be explained. By inputting input data acquired from the endoscopic image acquired by the image acquisition unit 261 into the operation selection model 265 according to the sixth exemplary embodiment for processing, the operation detail determination unit 262 determines one operation detail from among the twelve operation details for the operation of the endoscope 10.

The operation control unit 263 generates a movement control signal for executing control of advancing the insertion portion 11 at a speed of 5 cm/sec when the operation detail determined by the operation detail determination unit 262 is the push operation PSS_SH and outputs the movement control signal to the drive control unit 240. Thereby, the advancing and retracting control unit 241 generates an advancing and retracting control signal for advancing the insertion portion 11 at a speed of 5 cm/sec and drives the advancing and retracting mechanism 141. The time for the driving may be set to a predetermined time (for example, one second) in advance.

The operation control unit 263 generates a movement control signal for executing control of advancing the insertion portion 11 at a speed of 2 cm/sec when the operation detail determined by the operation detail determination unit 262 is the push operation PSS_SL and outputs the movement control signal to the drive control unit 240. Thereby, the advancing and retracting control unit 241 generates an advancing and retracting control signal for advancing the insertion portion 11 at a speed of 2 cm/sec and drives the advancing and retracting mechanism 141. The time for the driving may be set to a predetermined time in advance.

As described above, a label is set for a combination of a push operation for the insertion portion 11 and a movement speed due to the push operation and used for machine learning as training data in the sixth exemplary embodiment. With regard to the movement speed, push operations are classified into two classes. Alternatively, the push operations may be classified into three or more classes.

Further, a label may be set for a combination of not only a push operation but also an angle operation and a movement speed due to the angle operation and used for machine learning as training data. As described, in the sixth exemplary embodiment, training data in which a label is set for the combination of an operation detail and a movement speed in the operation detail is used so as to generate an operation selection model 265. Thereby, the operation detail and movement speed of the endoscope 10 can be easily determined by using the operation selection model 265.

Seventh Exemplary Embodiment

In the automatic insertion control of the endoscope 10, when the distal end 12 is advanced, control is preferably performed to stop or change the movement in progress according to resistance force (external force) from the intestinal tract applied to the distal end 12. If the external force acting on the distal end 12 is large, the distal end 12 may be pushing against a structure such as a fold. Thus, once the external force exceeds a predetermined control threshold, the advancing of the distal end 12 is stopped, and the distal end 12 is retracted. As described, a control threshold for stopping or changing the advancing movement is set for the advancing movement.

On the other hand, when intestinal stenosis is occurring, although the resistance force applied to the distal end 12 is high due to narrowing of the intestinal tract, the distal end 12 needs to be advanced for endoscopic observation. Therefore, in the seventh exemplary embodiment, an operation selection model 265 for realizing automatic insertion control of changing a control threshold of resistance force applied to the distal end 12 depending on whether or not stenosis is occurring is generated by machine learning.

An operation selection model 265 according to the seventh exemplary embodiment is a learned model generated through the learning of each coupling coefficient (weight) in CNN corresponding to a multilayer neural network including an input layer, one or more convolutional layers, an output layer by a learning method such as deep learning. In the generation of an operation selection model 265 according to the seventh exemplary embodiment, machine learning using training data that includes an image for learning, which is an endoscopic image of the inside of an intestine or a colon model imaged by an endoscope in the past, and a label indicating which of twelve operation details is most suitable for a situation shown by the image for learning.

The twelve operation details include an angle operation UPS, an angle operation DOS, an angle operation LES, an angle operation RIS, an angle operation URS, an angle operation ULS, an angle operation DLS, an angle operation DRS, a push operation PSS_TS in which relatively small resistance force is set as a control threshold for stopping the advancing, a push operation PSS_TL in which relatively large resistance force is set as the control threshold for stopping the advancing, a pull operation PLS, and a search operation SES.

At the time of generating the training data, a knowledgeable person looks at the image for learning, subjectively selects one operation detail that is most likely to be performed in a situation shown in the image for learning from among the twelve operation details described above, and assigns a label of the selected operation detail to the image for learning. This label assigning task is performed on a large number of past endoscopic images, thereby generating the training data.

Figure 18A:
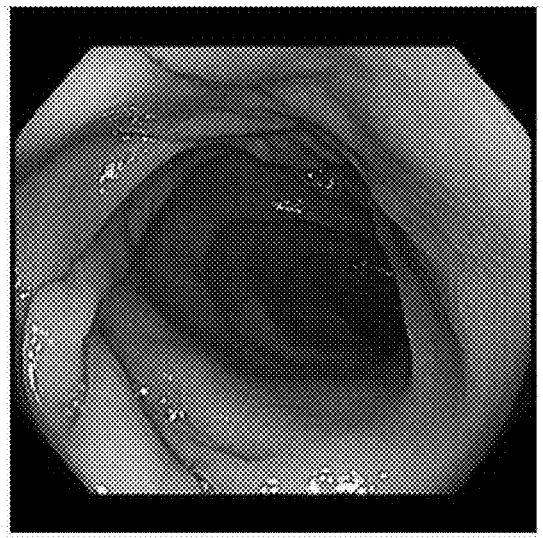
FIGS. 18A and 18B are diagrams showing examples of images for learning.
Figure 18B:
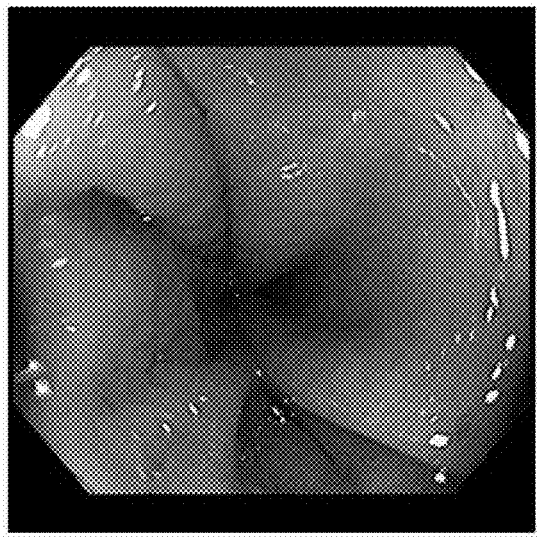

An example of training data including an image for learning and a label is shown below. FIG. 18A shows an image for learning of a lumen without stenosis, and FIG. 18B shows an image for learning of a lumen with stenosis. For all the images for learning shown in FIGS. 18A and 18B, a knowledgeable person also decides that the distal end 12 should be advanced as an endoscope operation to be performed next.

At this time, the knowledgeable person decides for the image for learning in FIG. 18A that advancing control may be performed on the insertion portion 11 using a normal control threshold. On the other hand, the knowledgeable person decides for the image for learning in FIG. 18B that the insertion portion 11 needs to be advanced while expanding the lumen with slightly strong advancing force and that the control threshold for stopping the advancing in normal advancing control is to be increased. Thus, in advancing control in which the advancing is stopped when resistance force F applied to the distal end 12 exceeds the control threshold, "push operation PSS_TS label" indicating a push operation with a control threshold set to F1 is assigned to the image for learning shown in FIG. 18A, and "push operation PSS_TL label" indicating a push operation with a control threshold set to F2 (>F1) is assigned to the image for learning shown in FIG. 18B.

In the third exemplary embodiment, "push operation PSS label" indicating a push operation is assigned to all the images for learning shown in FIG. 13. However, in the seventh exemplary embodiment, either one of "push operation PSS_TS label" and "push operation PSS_TL label" is assigned to the images for learning shown in FIG. 13. The operation selection model 265 according to the seventh exemplary embodiment is generated by machine learning using at least the training data sets shown in FIGS. 5 to 12, FIG. 14, FIG. 15, and FIG. 18.

The operation detail determination unit 262 determines one or more operation details by inputting input data acquired from an endoscopic image acquired in the image acquisition unit 261 to one or more into operation selection models 265 generated by machine learning using, as training data, an image for learning and a label indicating an operation detail for an endoscope that has imaged the image for learning. More specifically, the operation detail determination unit 262 acquires multidimensional data such as the pixel value of each pixel included in an endoscopic image acquired by the image acquisition unit 261 and inputs the multidimensional data as input data to an input layer of the neural network of the operation selection model 265. The operation selection model 265 according to the seventh exemplary embodiment outputs twelve likelihoods respectively corresponding to the twelve operation details that can be selected as the operation detail of the endoscope 10 from an output layer of the neural network. The operation detail determination unit 262 can obtain an operation detail corresponding to one likelihood that is the highest among the twelve likelihoods included in the output data as the result of selecting the operation detail of the endoscope 10.

The action of the seventh exemplary embodiment will now be explained. By inputting input data acquired from the endoscopic image acquired by the image acquisition unit 261 into the operation selection model 265 according to the sixth exemplary embodiment for processing, the operation detail determination unit 262 determines one operation detail from among the twelve operation details for the operation of the endoscope 10.

The operation control unit 263 generates a movement control signal for executing advancing control when the operation detail determined by the operation detail determination unit 262 is the push operation PSS_TS and outputs the movement control signal to the drive control unit 240. The operation control unit 263 monitors external force applied to the distal end 12 and outputs a signal indicating the stopping of the advancing control to the advancing and retracting control unit 241 when the external force exceeds F1.

The operation control unit 263 generates a movement control signal for executing advancing control when the operation detail determined by the operation detail determination unit 262 is the push operation PSS_TL and outputs the movement control signal to the drive control unit 240. The operation control unit 263 monitors external force applied to the distal end 12 and outputs a signal indicating the stopping of the advancing control to the advancing and retracting control unit 241 when the external force exceeds F2.

As described above, a label is set for a combination of a push operation for the insertion portion 11 and a control threshold according to the push operation and used for machine learning as training data in the seventh exemplary embodiment. With regard to the control threshold, push operations are classified into two classes. Alternatively, the push operations may be classified into three or more classes. Further, a label may be set for a combination of not only a push operation but also an angle operation and a control threshold in the angle operation and used for machine learning as training data.

Described above is an explanation on the present disclosure based on the embodiment and the exemplary embodiments. These embodiment and the exemplary embodiments are intended to be illustrative only, and it will be obvious to those skilled in the art that various modifications to constituting elements and processes could be developed and that such modifications are also within the scope of the present disclosure. The operation selection models 265 explained in the first through seventh exemplary embodiments can be used in combination with one another.

For example, explanations have been made that a label is set for the combination of an operation detail and an operation amount in the operation detail and used as training data in the fifth exemplary embodiment and that a label is set for the combination of an operation detail and a movement speed in the operation detail and used as training data in the sixth exemplary embodiment. In an exemplary variation, a label may be set for a combination of an operation detail, an operation amount and a movement speed and used as training data so as to generate an operation selection model 265.

Further, a first operation selection model 265a for determining an operation detail and a second operation selection model 265b for determining the operation amount (or movement speed) in the operation detail determined using the first operation selection model 265a may be generated, and the first operation selection model 265a and the second operation selection model 265b may be used in combination. In this case, the second operation selection model 265b may be generated using training data obtained by subdividing a training data group for each class used to generate the first operation selection model 265a.

In the embodiment, CNN, which is one of the most basic and stable methods in Deep Neural Network in recent years, has been explained as a learning model. Alternatively, more complex network models may be used. For example, in addition to endoscope images, it is also possible to build a multimodal network model that uses numerical endoscope insertion shape information as input. In this way, it is possible to realize control where not only an endoscopic image but also the insertion state of an endoscope is added to determination conditions.

In the exemplary embodiments, labels for an angle operation, a push operation, a pull operation, and a search operation are set. Alternatively, training data may be generated in which labels are set for "twist operation", "air feeding operation", "water feeding operation", and "suction operation" so as to generate an operation selection model 265 by machine learning.

The operation detail determination unit 262 may have a lumen depth direction detection unit that detects the lumen depth direction based on an endoscopic image acquired by the image acquisition unit 261 and an easy advancing direction decision unit that decides on a direction in which the advancing of the distal end is easier than other directions based on the endoscopic image. The operation detail determination unit 262 may determine the operation detail based on the result of the decision by the easy advancing direction decision unit and the result of the detection by the lumen depth direction detection unit.

Furthermore, the easy advancing direction decision unit may have an obstacle presence decision unit that decides on whether or not there is an obstacle that interferes the advancing when the advancing occurs in the lumen depth direction detected by the lumen depth direction detection unit, and the easy advancing direction decision unit may decide on a direction in which the advancing of the distal end of the endoscope is easier than other directions based on the result of the decision by the obstacle presence decision unit. In this case, examples of the obstacle is mucosa or fold of a lumen. For example, it may be decided that an obstacle exists if it is decided that mucosa and the distal end of the endoscope collide with each other at the time of the advancing in the lumen depth direction.

Of advancing directions without obstacles, a direction in which the advancing is easier than other directions is to be decided on. Regarding this, of the directions without obstacles, a direction in which the distal end of the endoscope has been advanced in the past according to the endoscopic image may be used as an easy advancing direction.

Further, the operation detail may be determined based on the angle between the direction decided on by the easy advancing direction decision unit and the direction detected by the lumen depth direction detection unit. For example, given that the angle between the direction decided on by the easy advancing direction decision unit and the direction detected by the lumen depth direction detection unit is denoted as an angle X, an angle Y in the advancing direction may be defined as Y=X/2, and the advancing may be carried out in the direction. In other words, the advancing may be carried out in a direction in which a bisector between the direction decided on by the easy advancing direction decision unit and the direction detected by the lumen depth direction detection unit is formed. Further, the advancing direction may be a direction indicated by a resultant vector obtained by combining the respective vectors of the direction decided on by the easy advancing direction decision unit and the direction detected by the lumen depth direction detection unit. Alternatively, the advancing may be carried out in the direction of a resultant vector C obtained by combining a direction vector A based on the result of the detection by the lumen depth direction detection unit and a direction vector B in the easy advancing direction decision unit. Furthermore, weighting a and b may be applied to the direction vectors A and B, respectively, and the advancing may be carried out in the direction of the resultant vector $C=\frac{1}{2}(a*A+b*B)$.

The operation detail determination unit 262 may have a lumen deep part shape recognition unit that recognizes the shape of the deep part of the lumen based on an endoscopic image acquired by the image acquisition unit 261 and determine the operation detail and the operation amount or movement speed in the operation detail based on the recognized shape of the deep part of the lumen. Further, the operation detail determination unit 262 may have an operation detail changing unit that changes the operation detail when the endoscope receives resistance force that is a predetermined control threshold or more, and based on the shape of the deep part of the lumen, the operation detail changing unit may change a control threshold for resistance force at which the operation detail changing unit changes the operation.

What is claimed is:

1. An endoscope control apparatus comprising:
   one or more processors comprising hardware, wherein the one or more processors are configured to:
   acquire an endoscopic image imaged by an endoscope;
   determine an operation detail from among a predetermined plural number of operation details by inputting input data acquired from the endoscopic image into an operation selection model generated by machine learning using, as a training data set, an image for learning, which is an endoscopic image imaged in the past, and a label that is assigned to the image for learning and that indicates an operation detail for an endoscope; and
   control a movement of the endoscope based on the determined operation detail,
   wherein the training data includes:
   first training data which includes a first image for learning in which the degree of bending of a large intestine has a first size and a first label indicating an operation of advancing the distal end of the endoscope by a first operation amount; and second training data which includes a second image for learning in which the degree of bending of the large intestine has a second size larger than the first size and a second label indicating an operation of advancing the distal end by a second operation amount smaller than the first operation amount, and wherein the one or more processors are further configured to:

obtain a selection result indicating one operation detail selected from among a plurality of operation details including an operation for advancing the distal end by the first operation amount and an operation for advancing the distal end by the second operation amount by inputting the input data into the operation selection model for processing.

2. An endoscope control apparatus comprising:

one or more processors comprising hardware, wherein the one or more processors are configured to:

acquire an endoscopic image imaged by an endoscope;

determine an operation detail from among a predetermined plural number of operation details by inputting input data acquired from the endoscopic image into an operation selection model generated by machine learning using, as a training data set, an image for learning, which is an endoscopic image imaged in the past, and a label that is assigned to the image for learning and that indicates an operation detail for an endoscope; and control a movement of the endoscope based on the determined operation detail, wherein the training data includes:

first training data which includes a first image for learning in which a part without abnormality is imaged and a first label indicating an operation of advancing the distal end of the endoscope at a first movement speed, and second training data which includes a second image for learning in which a part with an abnormality is imaged and a second label indicating an operation of advancing the distal end at a second movement speed slower than the first movement speed, and wherein the one or more processors are further configured to:

obtain a selection result indicating one operation detail selected from among a plurality of operation details including an operation for advancing the distal end at the first movement speed and an operation for advancing the distal end at the second movement speed by inputting the input data into the operation selection model for processing.

3. An endoscope control apparatus comprising:

one or more processors comprising hardware, wherein the one or more processors are configured to:

acquire an endoscopic image imaged by an endoscope;

determine an operation detail from among a predetermined plural number of operation details by inputting input data acquired from the endoscopic image into an operation selection model generated by machine learning using, as a training data set, an image for learning, which is an endoscopic image imaged in the past, and a label that is assigned to the image for learning and that indicates an operation detail for an endoscope; and control a movement of the endoscope based on the determined operation detail, wherein the training data includes:

first training data which includes a first image for learning in which a part without stenosis is imaged and a first label indicating an operation for executing first advancing control that advances the distal end of the endoscope and stops the advancing when external force applied to the distal end exceeds a first control threshold, and second training data which includes a second image for learning in which a part with stenosis is imaged and a second label indicating an operation for executing second advancing control that advances the distal end and stops the advancing when the external force applied to the distal end exceeds a second control threshold larger than the first control threshold, and wherein the one or more processors are configured to:

obtain a selection result indicating one operation detail selected from among a plurality of operation details including an operation for executing the first advancing control and an operation for executing the second advancing control, by inputting the input data into the operation selection model for processing.

* * * * *